(12) United States Patent
Beckman et al.

(10) Patent No.: US 12,329,486 B2
(45) Date of Patent: Jun. 17, 2025

(54) DRIVE CABLE ACCUMULATION SYSTEMS FOR ROBOTIC SURGICAL TOOLS

(71) Applicant: Cilag GmbH International, Zug (CH)

(72) Inventors: Andrew T. Beckman, Cincinnati, OH (US); Spencer James Witte, San Francisco, CA (US); Charles J. Scheib, Loveland, OH (US); Benjamin D. Dickerson, San Francisco, CA (US); Travis Michael Schuh, Los Altos, CA (US); Eric N. Johnson, Maineville, OH (US); Jason Alan Hill, Loveland, OH (US)

(73) Assignee: Cilag GmbH International, Zug (CH)

( * ) Notice: Subject to any disclaimer, the term of this patent is extended or adjusted under 35 U.S.C. 154(b) by 1186 days.

(21) Appl. No.: 17/153,026

(22) Filed: Jan. 20, 2021

(65) Prior Publication Data
US 2022/0226056 A1  Jul. 21, 2022

(51) Int. Cl.
*A61B 34/00* (2016.01)
*A61B 17/295* (2006.01)
*B25J 9/10* (2006.01)
*B25J 15/00* (2006.01)

(52) U.S. Cl.
CPC .......... *A61B 34/71* (2016.02); *A61B 17/295* (2013.01); *B25J 9/1035* (2013.01); *B25J 9/1045* (2013.01); *B25J 15/0028* (2013.01); *A61B 2034/715* (2016.02)

(58) Field of Classification Search
CPC .............. A61B 34/71; A61B 2034/715; A61B 17/29–17/295; A61B 17/068–17/07292; A61B 34/70; A61B 34/30–34/77; B25J 9/1035; B25J 9/1045; B25J 15/0028
See application file for complete search history.

(56) References Cited

U.S. PATENT DOCUMENTS

| 2019/0175287 A1* | 6/2019 | Hill | ..................... A61B 1/0016 |
| 2019/0201149 A1* | 7/2019 | Ito | .......................... A61B 34/30 |
| 2021/0015572 A1 | 1/2021 | Gomez et al. | |
| 2021/0022815 A1 | 1/2021 | Abbott | |

* cited by examiner

*Primary Examiner* — Elizabeth Houston
*Assistant Examiner* — Daniel Icet
(74) *Attorney, Agent, or Firm* — Vorys, Sater, Seymour and Pease LLP

(57) ABSTRACT

A robotic surgical tool includes a handle providing a drive input, an elongate shaft extendable through the handle and having an end effector arranged at a distal end of the shaft, and an accumulator system housed within the handle and operatively coupled to the drive input such that actuation of the drive input operates the accumulator system. At least one drive cable is threaded through the accumulator system and extends distally along the shaft, wherein operation of the accumulator system acts on the at least one drive cable to operate the end effector.

14 Claims, 23 Drawing Sheets

DRIVE CABLE ACCUMULATION SYSTEMS FOR ROBOTIC SURGICAL TOOLS

TECHNICAL FIELD

The systems and methods disclosed herein are directed to robotic surgical tools and, more particularly to, cable-based accumulation systems that cause end effector operation.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar are used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, suction irrigators, blades (i.e., RF), and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation and allows for access to hard to reach spaces. The instrument's end effector can be articulated (moved) using motors and actuators forming part of a computerized motion system. A user (e.g., a surgeon) is able to remotely operate an instrument's end effector by grasping and manipulating in space one or more controllers that communicate with an instrument driver coupled to the surgical instrument. User inputs are processed by a computer system incorporated into the robotic surgical system and the instrument driver responds by actuating the motors and actuators of the motion system. Moving drive cables, rods, and/or other mechanical mechanisms causes the end effector to articulate to desired positions and configurations.

Improvements to robotically-enabled medical systems will provide physicians with the ability to perform endoscopic and laparoscopic procedures more effectively and with improved ease.

SUMMARY OF DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

Embodiments disclosed herein include a robotic surgical tool that includes a handle providing a drive input, an elongate shaft extendable through the handle and having an end effector arranged at a distal end of the shaft, an accumulator system housed within the handle and operatively coupled to the drive input such that actuation of the drive input operates the accumulator system, and at least one drive cable threaded through the accumulator system and extending distally along the shaft, wherein operation of the accumulator system alters at least one of a length or a force in the at least one drive cable to affect end effector operation. In a further embodiment, the robotic surgical tool includes an instrument driver arranged at an end of a robotic arm and matable with the handle, wherein the instrument driver provides a drive output matable with the drive input, and wherein the shaft extends through the instrument driver via a central aperture defined longitudinally through the instrument driver. In another further embodiment, the robotic surgical tool further includes an articulable wrist interposing the end effector and the distal end of the shaft, wherein the at least one drive cable is operatively coupled to the wrist and operation of the accumulator system acts on the at least one drive cable to articulate the end effector via the wrist. In another further embodiment, the robotic surgical tool further includes opposing jaws that form part of the end effector, and a knife drive system arranged at the distal end of the shaft and including a knife, wherein the at least one drive cable is operatively coupled to the knife drive system and operation of the accumulator system acts on the at least one drive cable to advance or retract the knife along the opposing jaws. In another further embodiment, the accumulator system further comprises a first pulley and a second pulley offset from the first pulley, and wherein actuation of the drive input moves the first pulley towards or away from the second pulley. In another further embodiment, the at least one drive cable comprises first and second drive cables and the accumulator system further comprises a lead screw extending from the drive input, a nut threadably mounted to the lead screw such that rotation of the lead screw causes the nut to axially traverse the lead screw, and first and second idler pulleys rotatably mounted to the handle and longitudinally spaced from each other, wherein the first pulley is rotatably mounted to the nut, and the second pulley is rotatably mounted to the handle and axially offset from the first pulley, wherein movement of the nut along the lead screw moves the first pulley toward or away from the second pulley, and wherein the first drive cable is guided through the first and second pulleys and the first and second idler pulleys, and wherein the second drive cable is guided through the first and second pulleys. In another further embodiment, the accumulator system further comprises one or more channel guides defined by the nut, and one or more opposing guide structures provided by the handle and engageable with the one or more channel guides, wherein receiving the one or more opposing guide structures in the one or more channel guides prevents the nut from rotating as the lead screw rotates. In another further embodiment, proximal movement of one unit of length of the nut along the lead screw results in more than one unit of length of the first drive cable being paid out from the accumulator system to the shaft, and more than one unit of length of the second drive cable being paid in to the accumulator system from the shaft, and wherein distal movement of one unit of length of the nut along the lead screw results in more than one unit of length of the second drive cable being paid out from the accumulator system to the shaft, and more than one unit of length of the first drive cable being paid in to the accumulator system from the shaft. In another further embodiment, a first end of the first drive cable is anchored to the shaft distal to the handle and a first end of the second drive cable is anchored to the shaft proximal to the handle, wherein a second end of the first drive cable extends proximally toward a proximal end of the shaft where it loops around a shaft pulley and extends distally toward the end effector, and wherein a second end of the second drive cable extends distally toward the end effector. In another further embodiment, the accumulator system further comprises a beveled pinion gear coupled to the drive input, a bevel gear arranged to intermesh with the beveled pinion gear, and one or more accumulator pulleys rotatably coupled to the bevel gear, wherein the at least one drive cable is routed from the shaft, through the one or more accumulator pulleys, and back to the shaft, and wherein rotation of the bevel gear in a first angular direction pays in a portion of the at least one drive cable from the shaft, and rotation of the bevel gear in a second angular direction pays out a portion of the at least one drive cable to the shaft. In another further embodiment, the bevel gear comprises a first bevel gear and the one or more accumulator pulleys comprise one or more first accumulator pulleys, the accumulator system further comprising a second bevel gear laterally offset from the first bevel gear and arranged to intermesh with the beveled pinion gear, one or more second accumulator pulleys rotatably coupled to the second bevel gear, wherein the at least one drive cable is routed from the shaft, through the first and second accumulator pulleys, and back to the shaft, and wherein rotation of the beveled pinion gear causes the first and second bevel gears to rotate in opposite angular directions. In another further embodiment, the at least one drive cable comprises first and second drive cable portions extending distally along the shaft, and wherein rotation of the beveled pinion gear in a first direction pays in a length of the first drive cable portion to the one or more first accumulator pulleys from the shaft, and simultaneously pays out a length of the second drive cable portion from the one or more second accumulator pulleys and to the shaft. In another further embodiment, the at least one drive cable comprises first and second drive cables and the drive input comprises a first drive input, the accumulator system further comprising a first beveled pinion gear coupled to the first drive input, a first bevel gear arranged to intermesh with the first beveled pinion gear, a second beveled pinion gear coupled to a second drive input rotatably mounted to the handle, a second bevel gear arranged to intermesh with the second beveled pinion gear, and one or more first accumulator pulleys rotatably coupled to the first bevel gear, and one or more second accumulator pulleys rotatably coupled to the second bevel gear, wherein the first drive cable is routed from the shaft, through the one or more first accumulator pulleys, and back to the shaft, and the second drive cable is routed from the shaft, through the one or more second accumulator pulleys, and back to the shaft, and wherein rotation of the first bevel gear in a first angular direction pays in a portion of the at first drive cable from the shaft, and rotation of the second bevel gear in a second angular direction pays out a portion of the second drive cable to the shaft.

Embodiments disclosed herein may further include a method of operating a robotic surgical tool that includes actuating a drive input of a robotic surgical tool, the robotic surgical tool having an elongate shaft extending through a handle that provides the drive input, an accumulator system housed within the handle and operatively coupled to the drive input, and at least one drive cable threaded through the accumulator system and extending distally along the shaft. The method may further include operating the accumulator system by actuating the drive input and thereby moving the at least one drive cable along the shaft and altering at least one of a length or a force in the at least one drive cable, and operating an end effector arranged at a distal end of the shaft with movement of the at least one drive cable. In a further embodiment, the handle is matable with an instrument driver arranged at an end of a robotic arm and the instrument driver provides a drive output, and wherein actuating the drive input comprises actuating the drive output mated with the drive input. In another further embodiment, the robotic surgical tool further includes an articulable wrist interposing the end effector and the distal end of the shaft and the at least one drive cable is operatively coupled to the wrist, and wherein operating the end effector further comprises placing tension on the at least one drive cable via operation of the accumulator system, and articulating the end effector based on the tension assumed by the at least one drive cable. In another further embodiment, the robotic surgical tool further includes opposing jaws that form part of the end effector and a knife drive system arranged at the distal end of the shaft and including a knife, and wherein operating the end effector further comprises placing tension on the at least one drive cable via the accumulator system, the at least one cable being operatively coupled to the knife drive system, and advancing or retracting the knife along the opposing jaws based on the tensile load assumed by the at least one drive cable. In another further embodiment, the at least one drive cable comprises first and second drive cables, the accumulator system comprises a lead screw extending from the drive input, a nut threadably mounted to the lead screw, a first pulley rotatably mounted to the nut, a second pulley rotatably mounted to the handle, and first and second idler pulleys rotatably mounted to the handle, and wherein operating the accumulator system comprises rotating the lead screw as the drive input rotates, moving the nut along the lead screw as the lead screw rotates and thereby moving the first pulley toward or away from the second pulley, coursing the first drive cable through the first and second pulleys and the first and second idler pulleys as the nut moves, coursing the second drive cable through the first and second pulleys as the nut moves. In another further embodiment, the method further includes moving the nut proximally one unit of length along the lead screw and thereby paying out more than one unit of length of the first drive cable from the accumulator system to the shaft, and paying in more than one unit of length of the second drive cable into the accumulator system from the shaft, and moving the nut distally one unit of length along the lead screw and thereby paying out more than one unit of length of the second drive cable from the accumulator system to the shaft, and paying in more than one unit of length of the first drive cable into the accumulator system from the shaft. In another further embodiment, the accumulator system includes a beveled pinion gear coupled to the drive input, a bevel gear arranged to intermesh with the beveled pinion gear, and one or more accumulator pulleys rotatably coupled to the bevel gear, and wherein operating the accumulator system comprises rotating the beveled pinion gear as the drive input rotates, rotating the bevel gear with rotation of the beveled pinion gear, wherein the at least one drive cable is routed from the shaft, through the one or more accumulator pulleys, and back to the shaft, drawing in a portion of the at least one drive cable from the shaft and simultaneously dispensing a portion of the at least one drive cable to the shaft as the bevel gear rotates. In another further embodiment, the method further includes moving the shaft relative to the handle while simultaneously operating the accumulator system.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance, to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto, as such concepts may have applicability throughout the entire specification.

A. Robotic System—Cart

Figure 1:
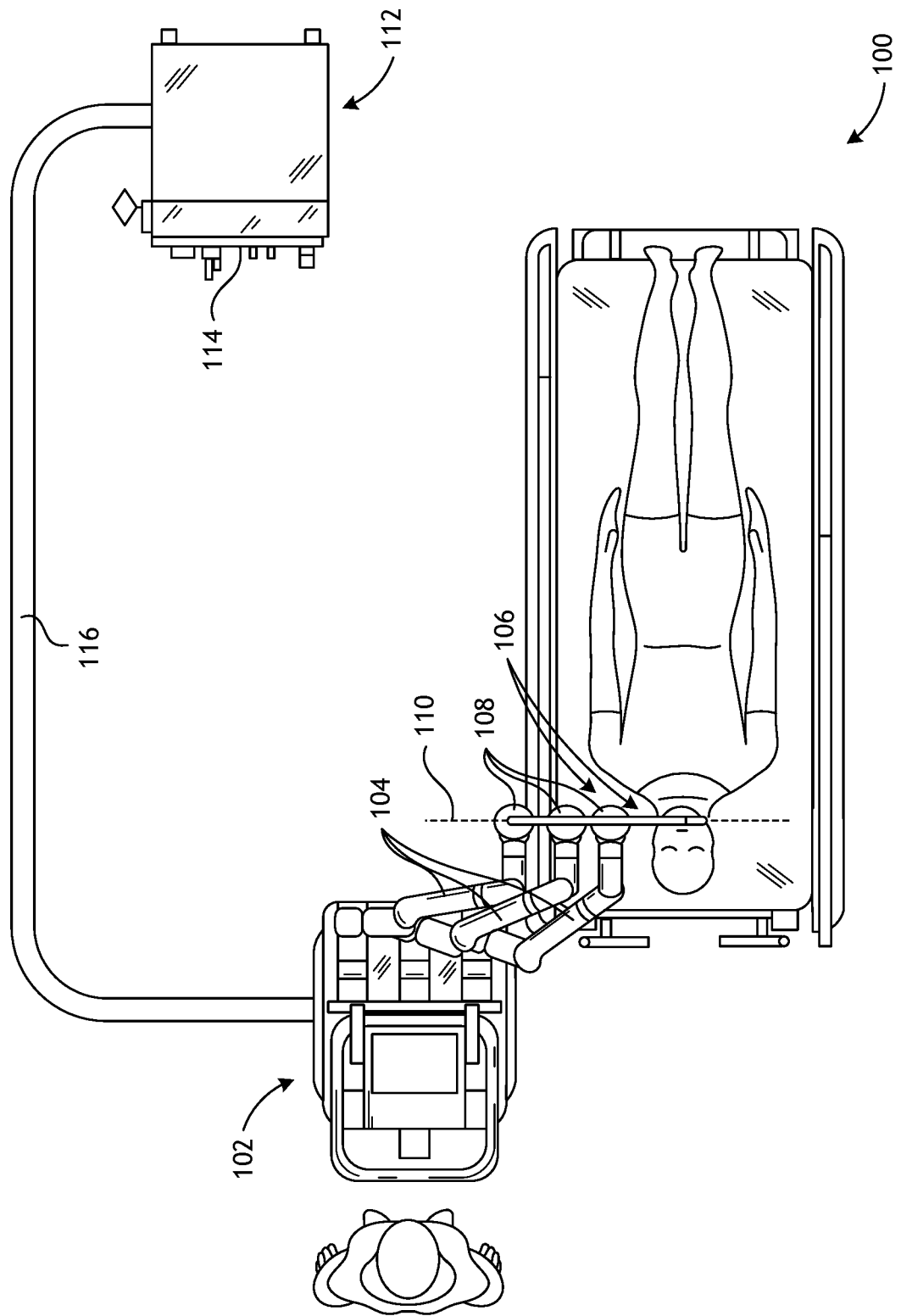
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastro-intestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or re-positioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
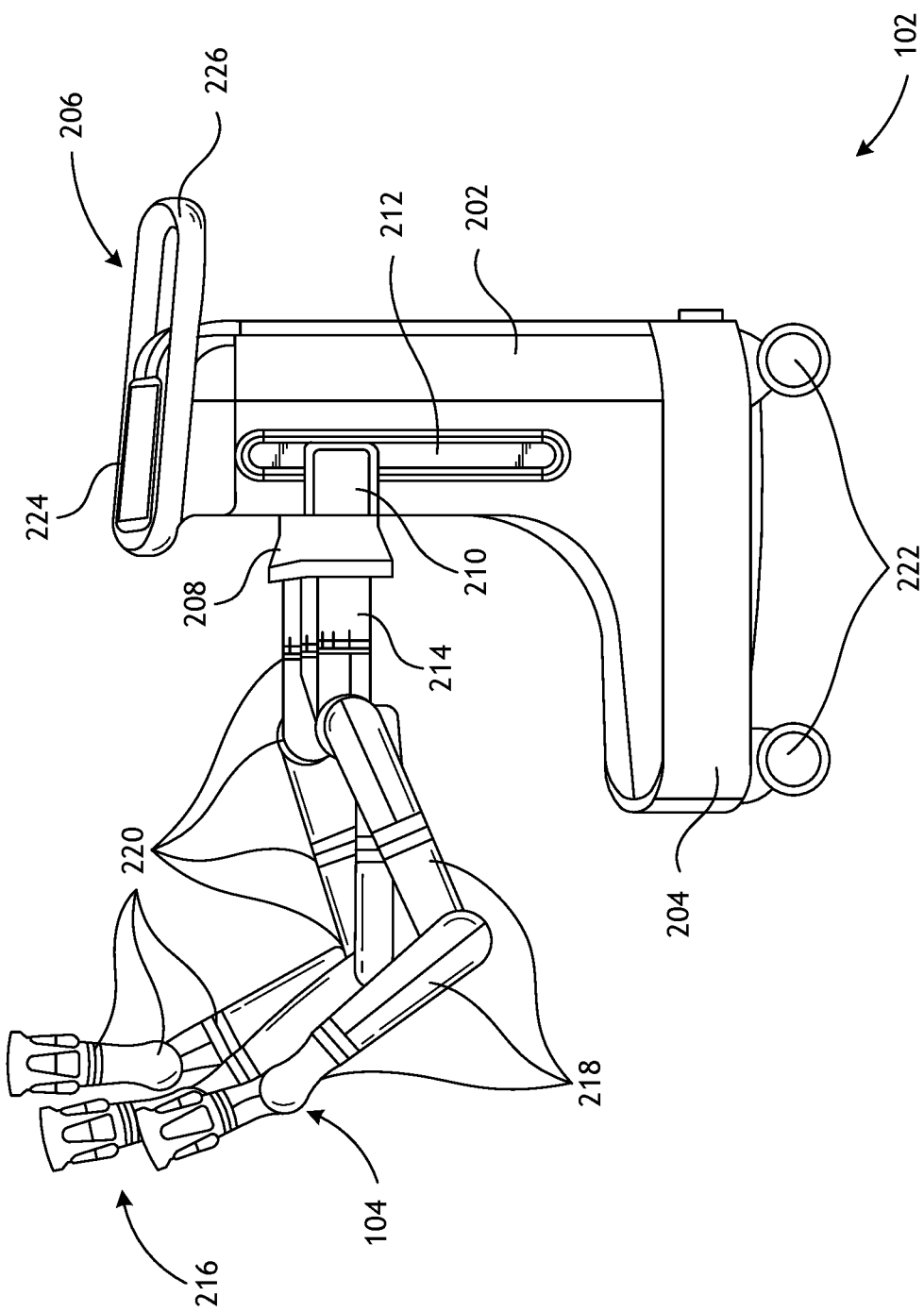
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, which are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, the carriage 208, and the arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
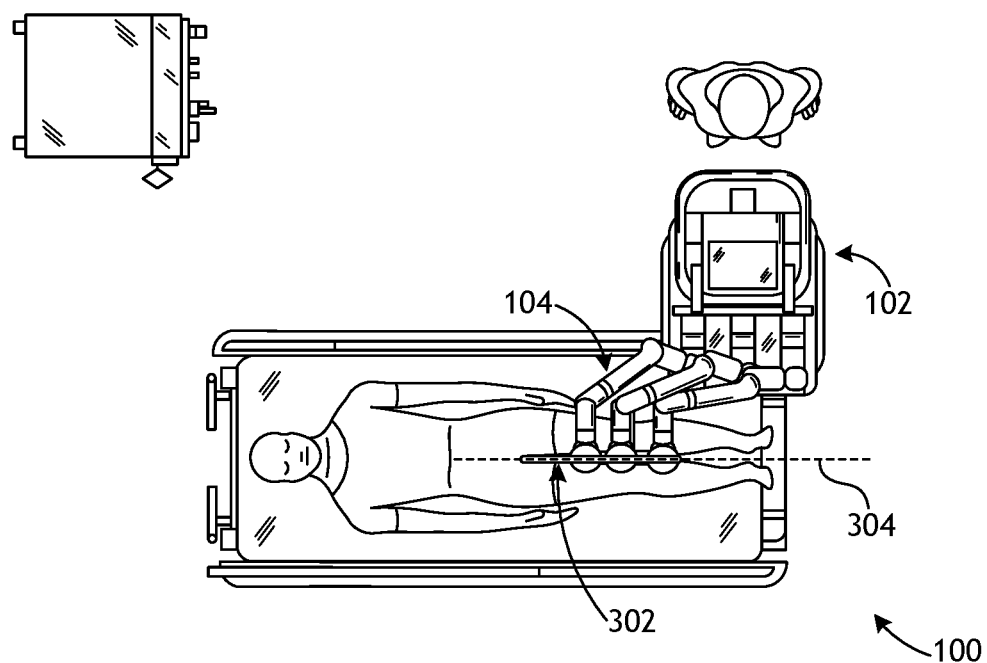
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
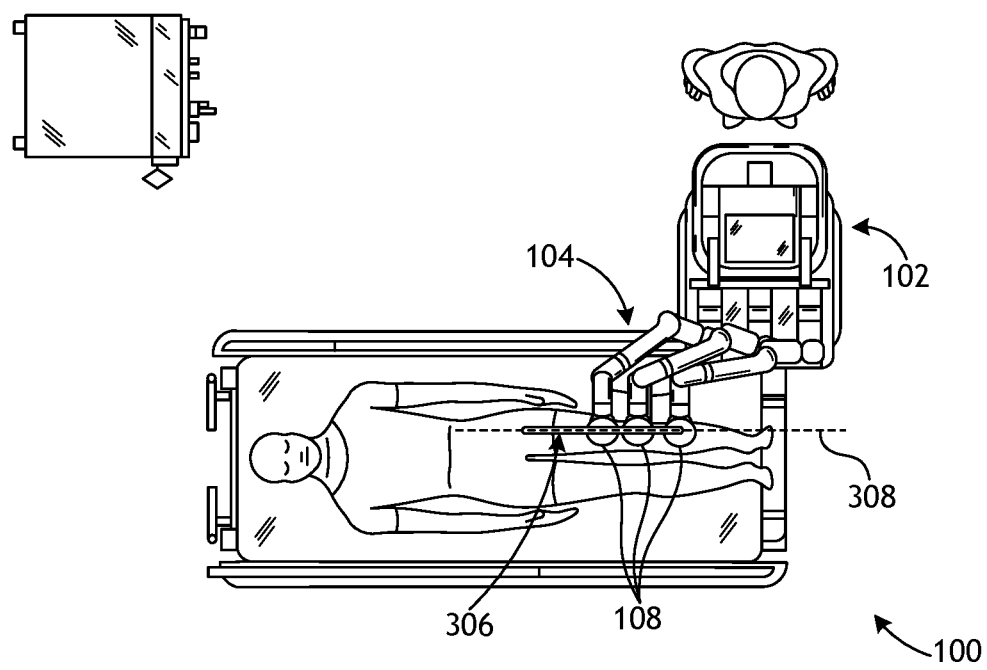
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table

Figure 4:
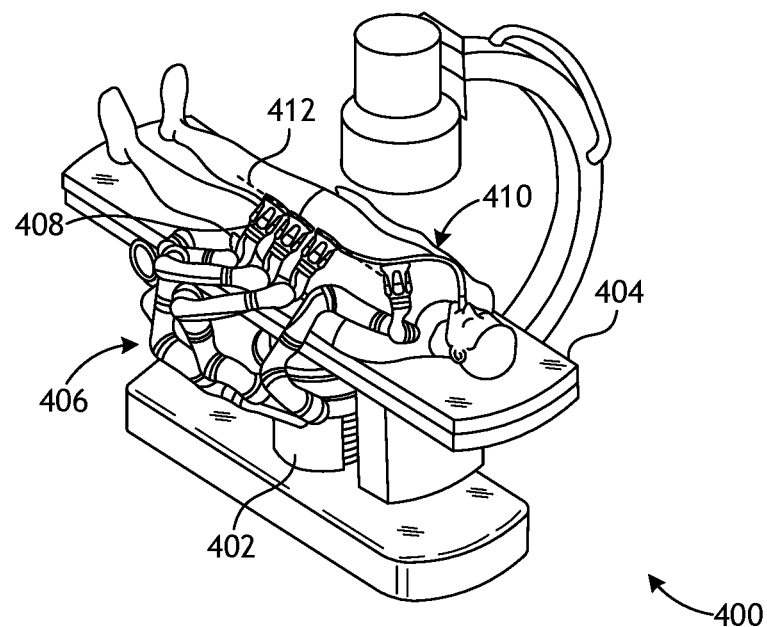
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
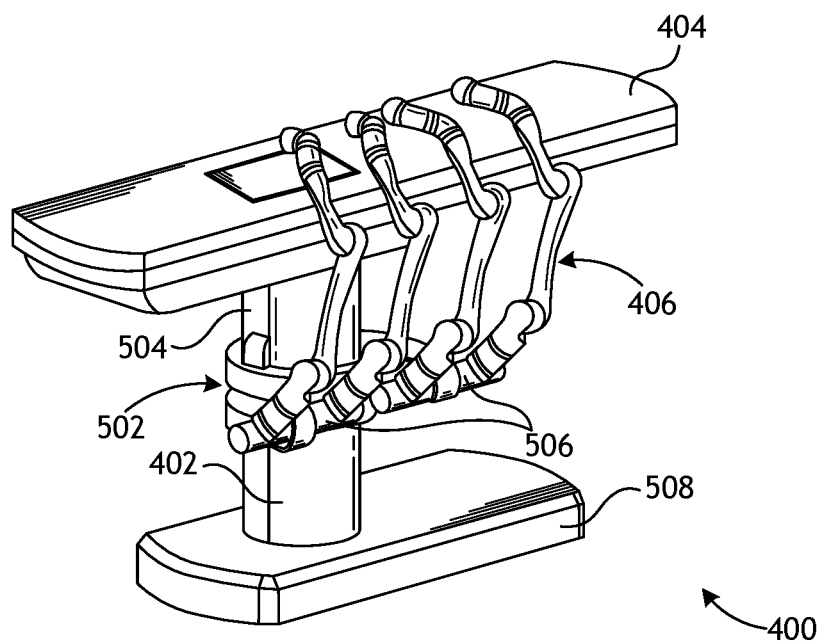
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
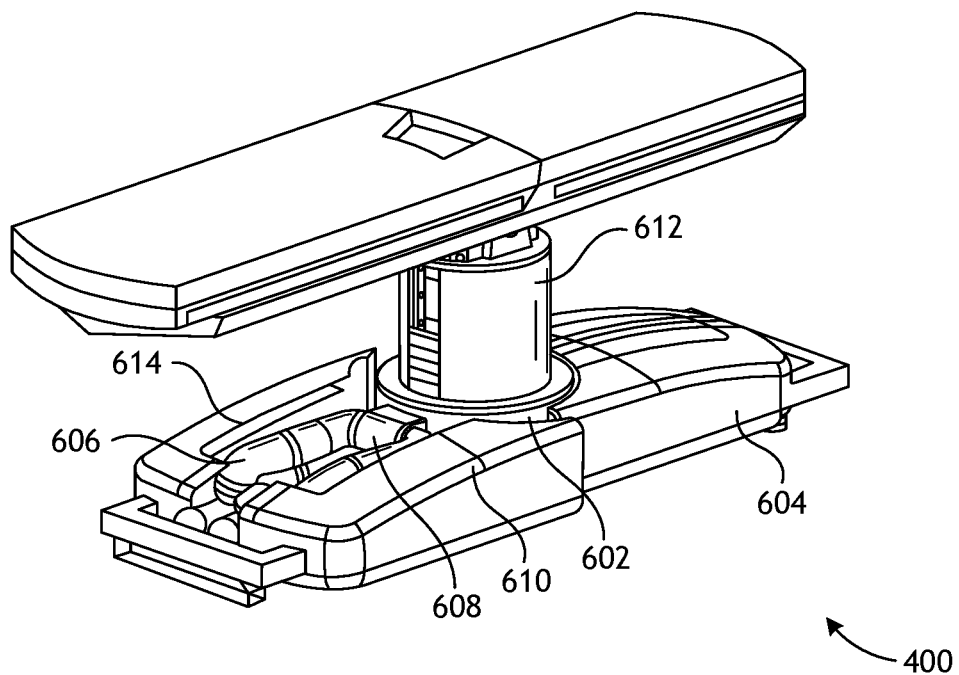
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
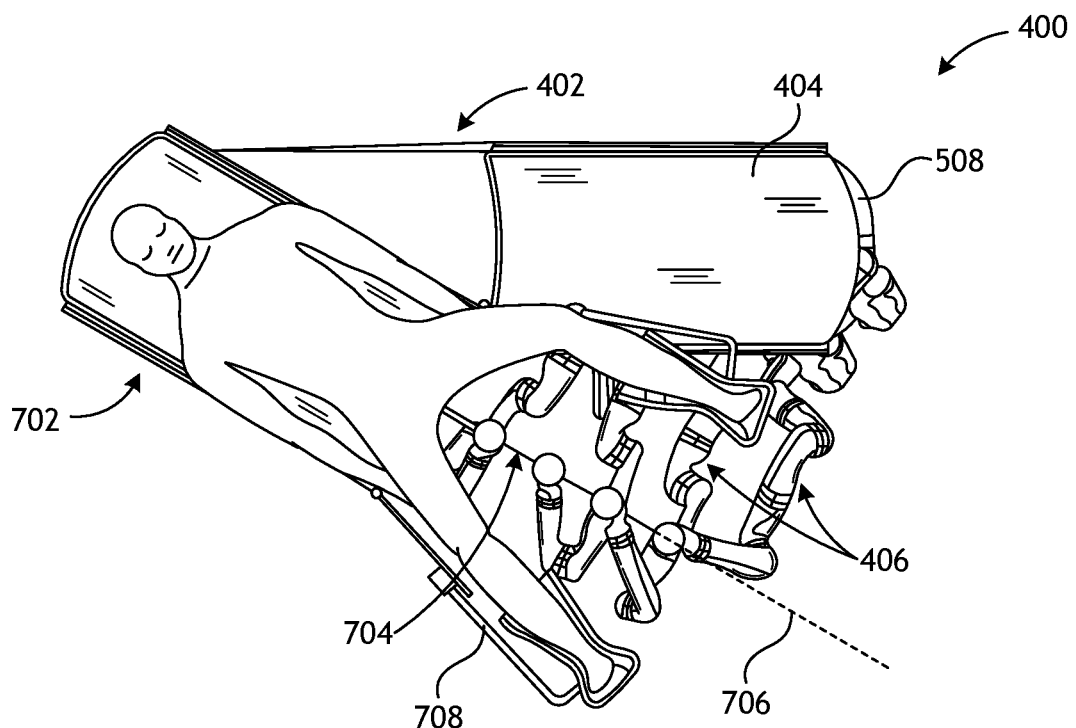
FIG. 7A illustrates an embodiment of a table-based robotic system configured for a ureteroscopy procedure.
Figure 7B:
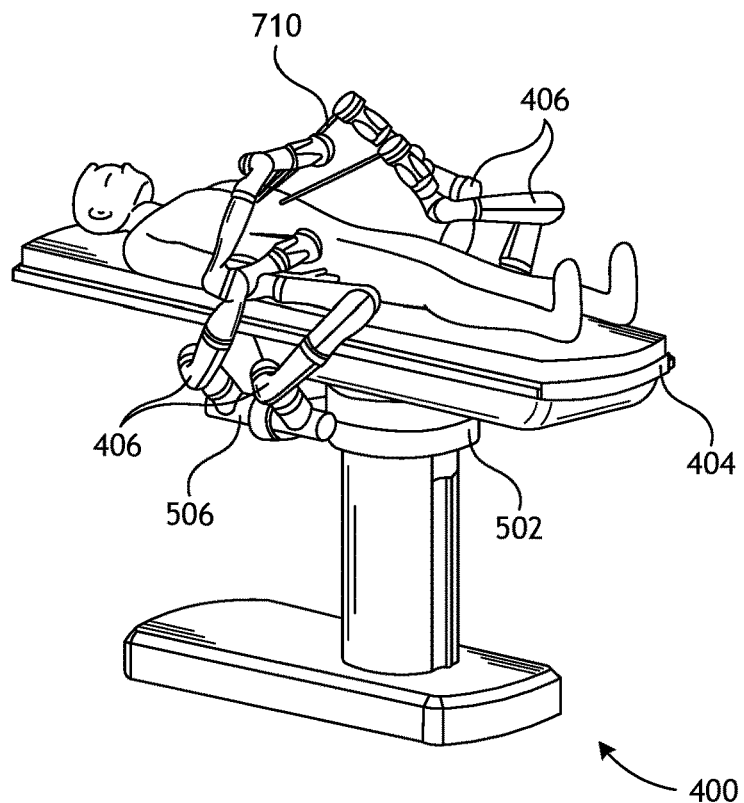
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
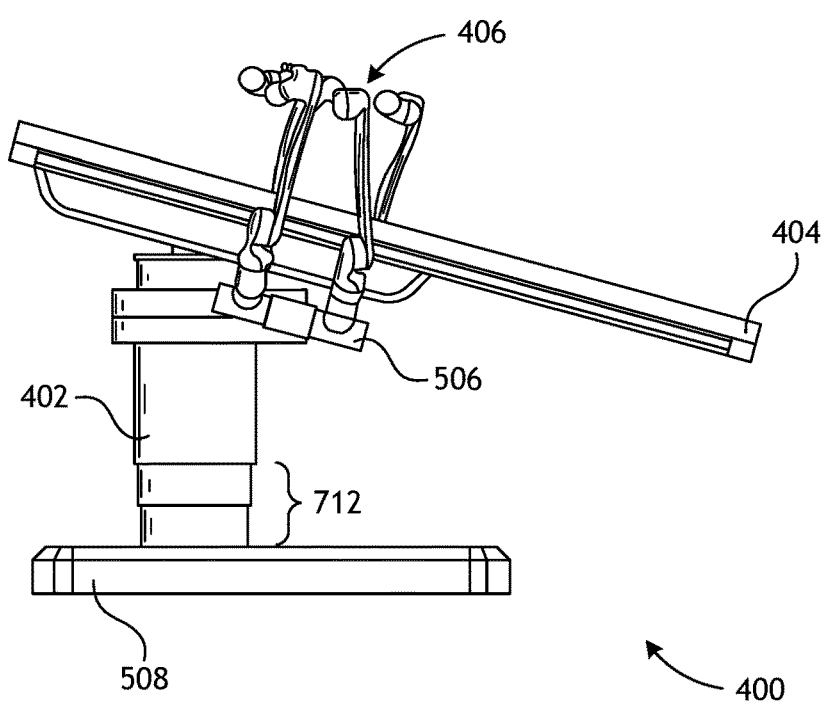
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
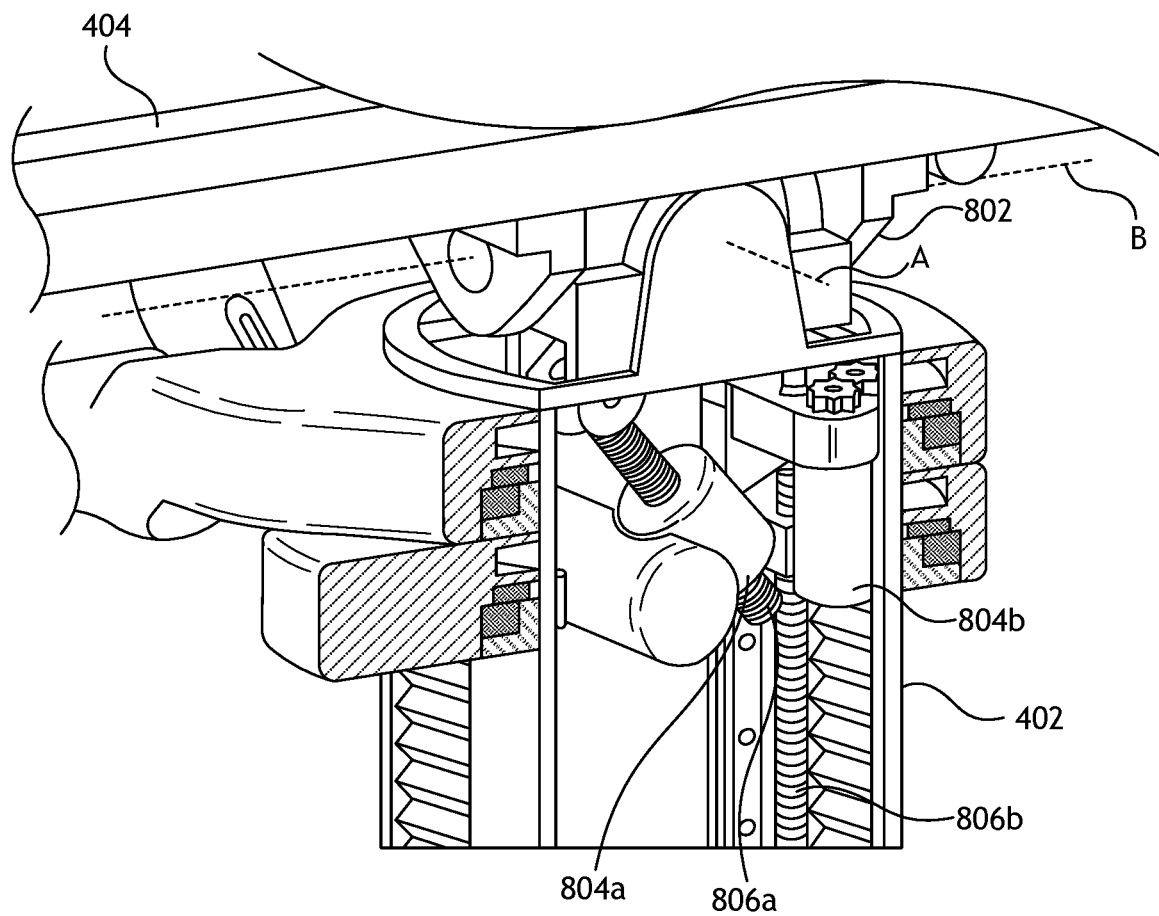
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804*a* and 804*b* responsive to an electrical pitch angle command. Rotation along one screw 806*a* would enable tilt adjustments in one axis A, while rotation along another screw 806*b* would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
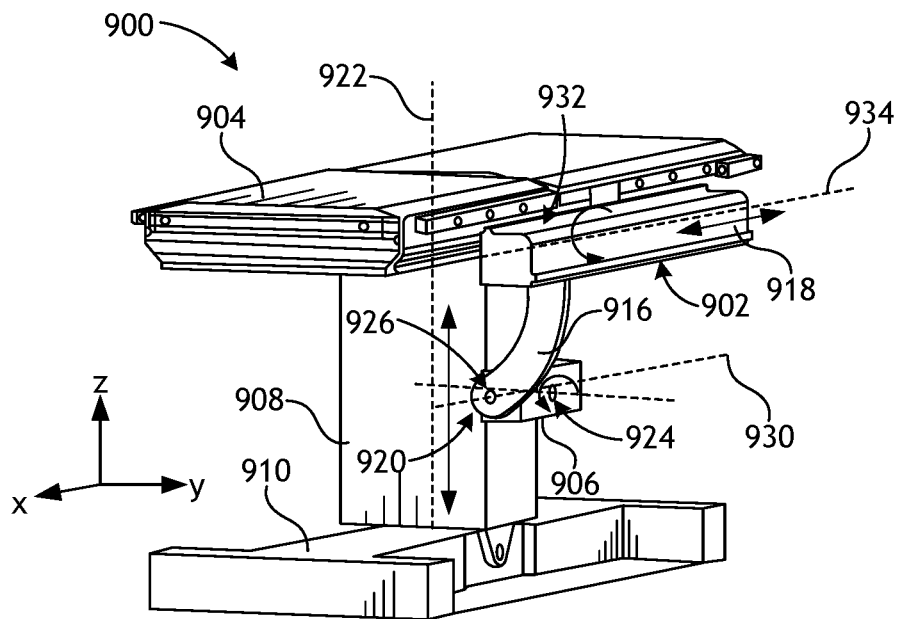
FIG. 9A illustrates an alternative embodiment of a table-based robotic system.
Figure 9B:
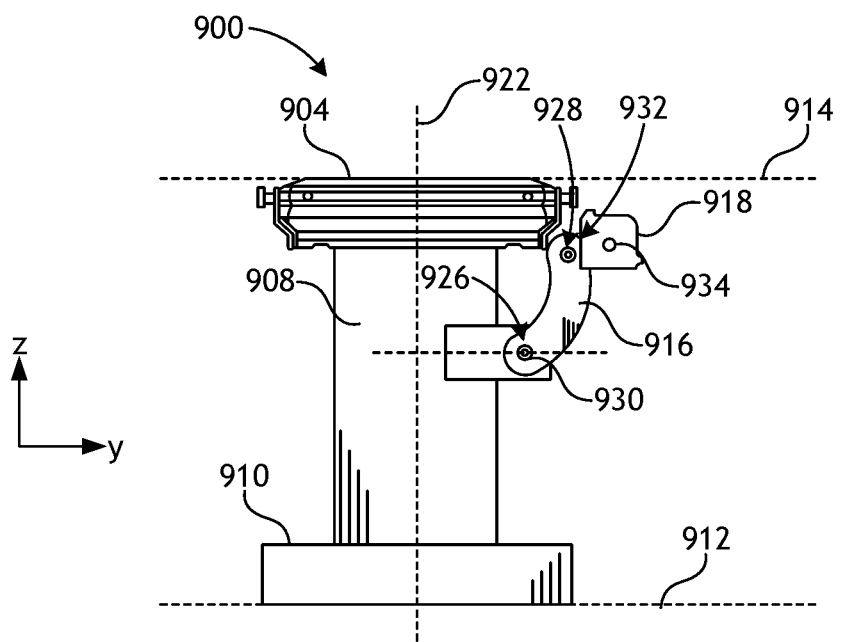
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
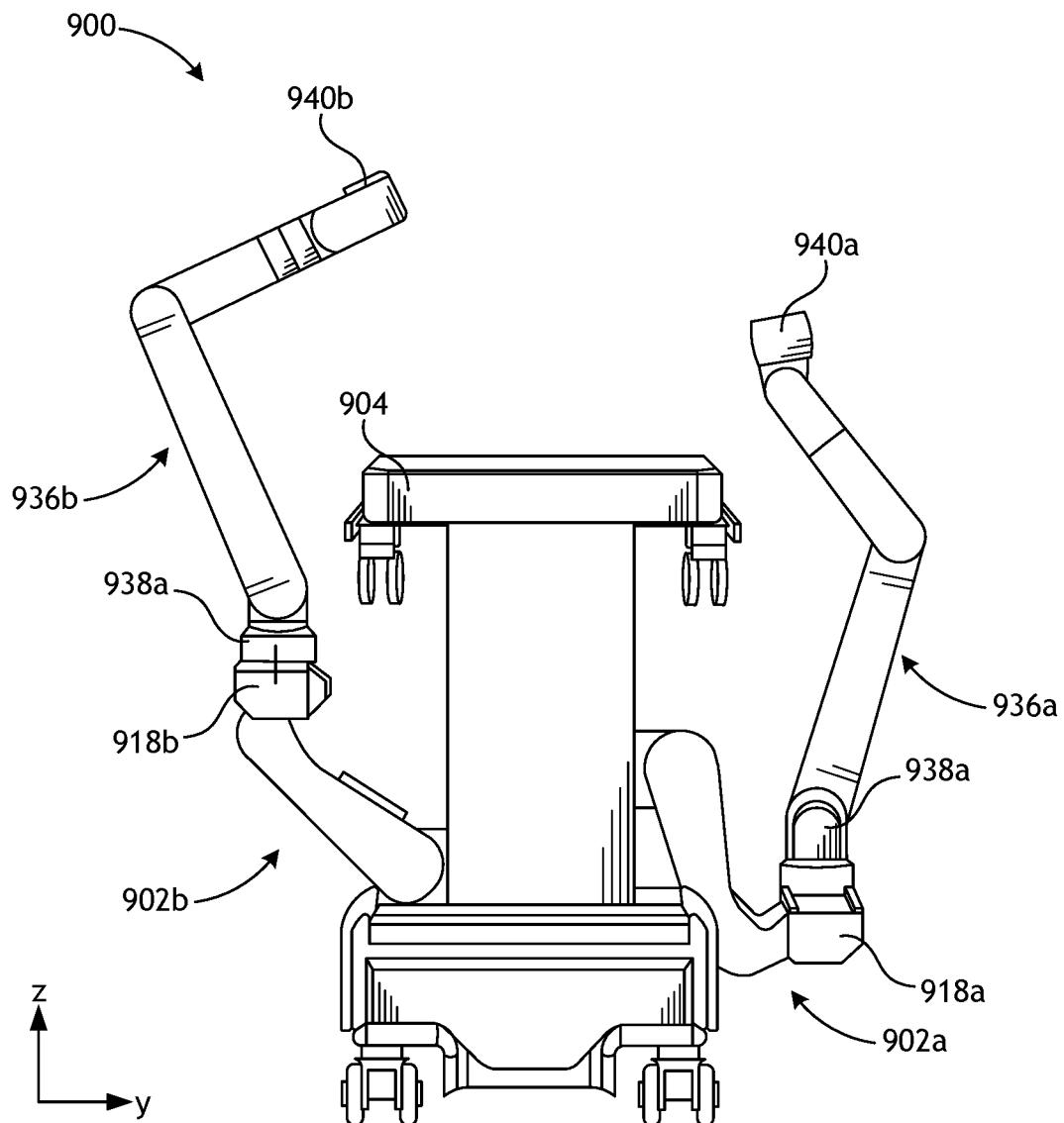
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface

The end effectors of a system's robotic arms comprise (i) an instrument driver (alternatively referred to as "tool driver," "instrument drive mechanism," "instrument device manipulator," and "drive input") that incorporate electro-mechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
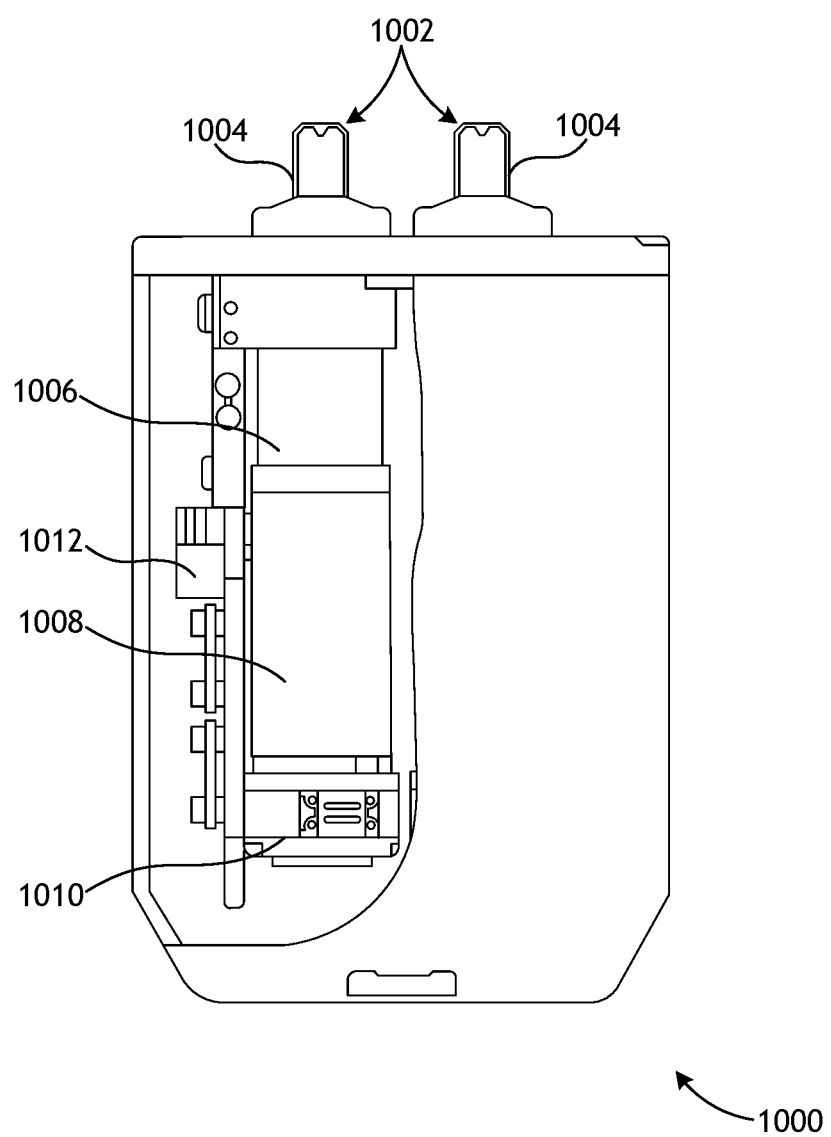
FIG. 10 illustrates an exemplary instrument driver.

FIG. 10 illustrates an example instrument driver 1000, according to one or more embodiments. Positioned at the distal end of a robotic arm, the instrument driver 1000 includes one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independently controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument

Figure 11:
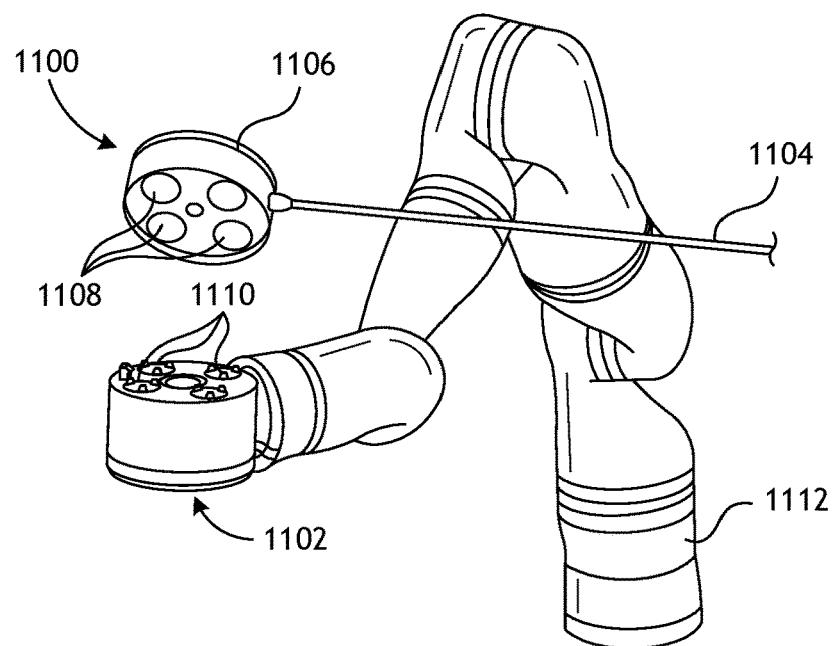
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
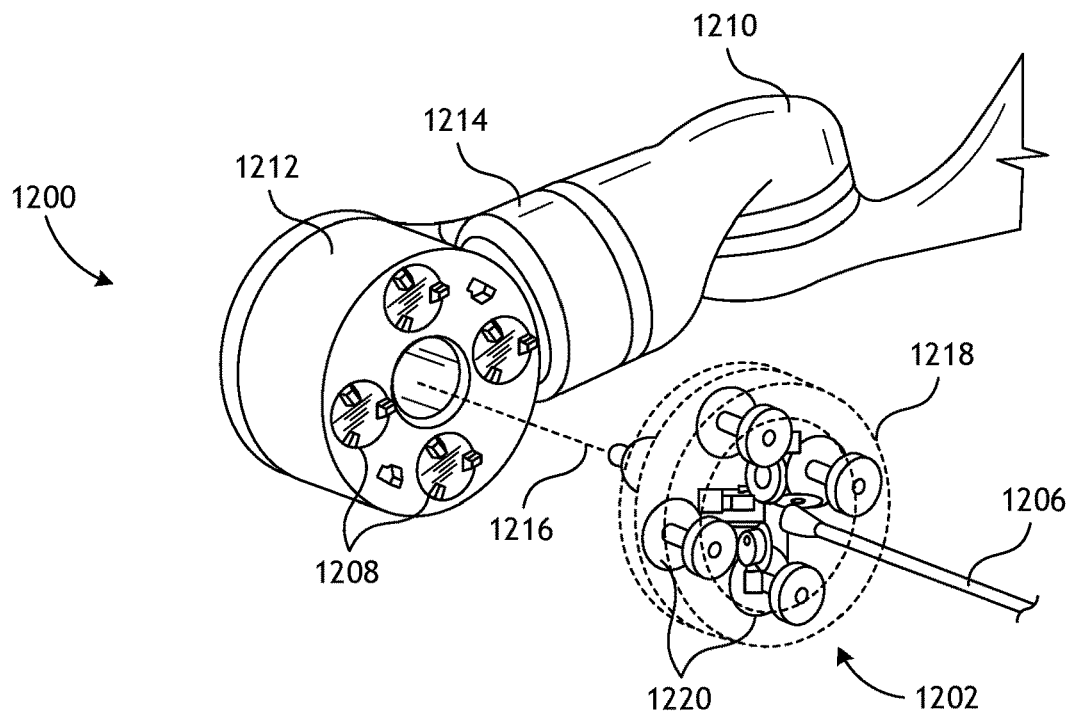
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
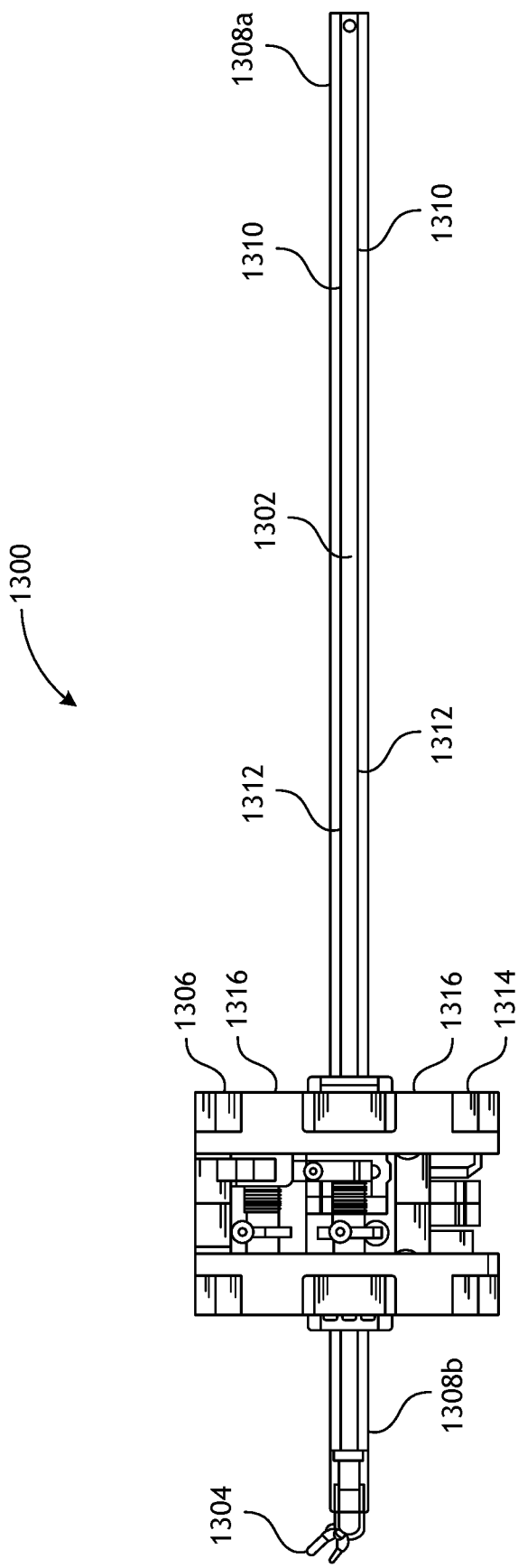
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308a and a distal portion 1308b. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument 1300, thereby minimizing the reliance on a robot arm to provide insertion of the instrument 1300. In other embodiments, a robotic arm can be largely responsible for instrument insertion.

E. Controller

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
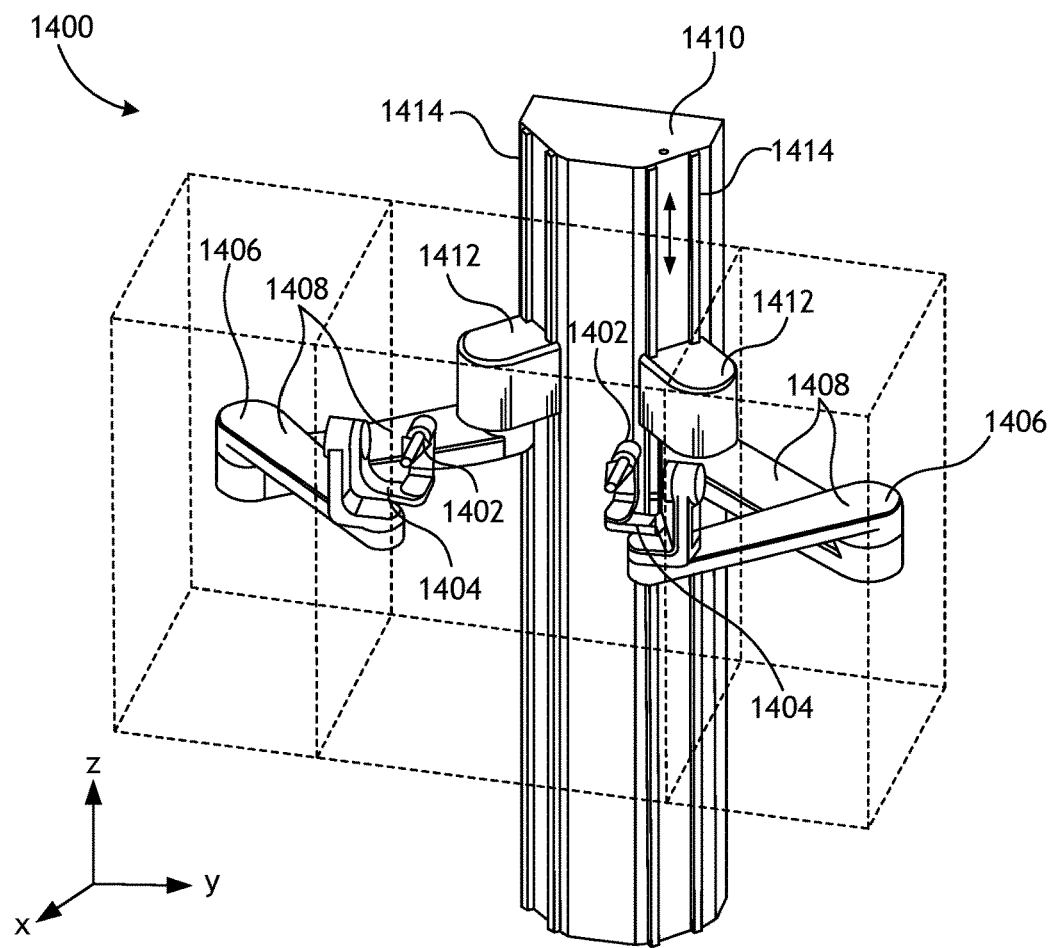
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
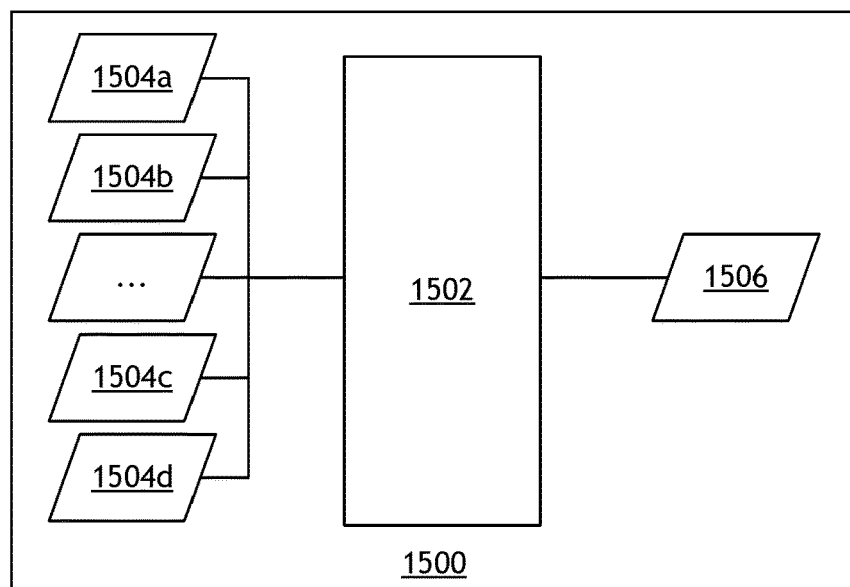
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504*a*, 1504*b*, 1504*c*, and 1504*d* to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504*a-d* are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504*a* (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504*b*. The localization module 1502 may process the vision data 1504*b* to enable one or more vision-based location tracking. For example, the preoperative model data may be used in conjunction with the vision data 1504*b* to enable computer vision-based tracking of the medical instrument (e.g., an endoscope or an instrument advance through a working channel of the endoscope). For example, using the preoperative model data 1504*a*, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504*a* that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504*b* to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504*c*. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504*d* may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504*a-d* in combination(s). In some cases, such a combination may use a probabilistic approach where the localization module 1502 assigns a confidence weight to the location determined from each of the input data 1504*a-d*. Thus, where the EM data 1504*c* may not be reliable (as may be the case where there is EM interference) the confidence of the location determined by the EM data 1504*c* can be decrease and the localization module 1502 may rely more heavily on the vision data 1504*b* and/or the robotic command and kinematics data 1504*d*.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Description

Figure 16:
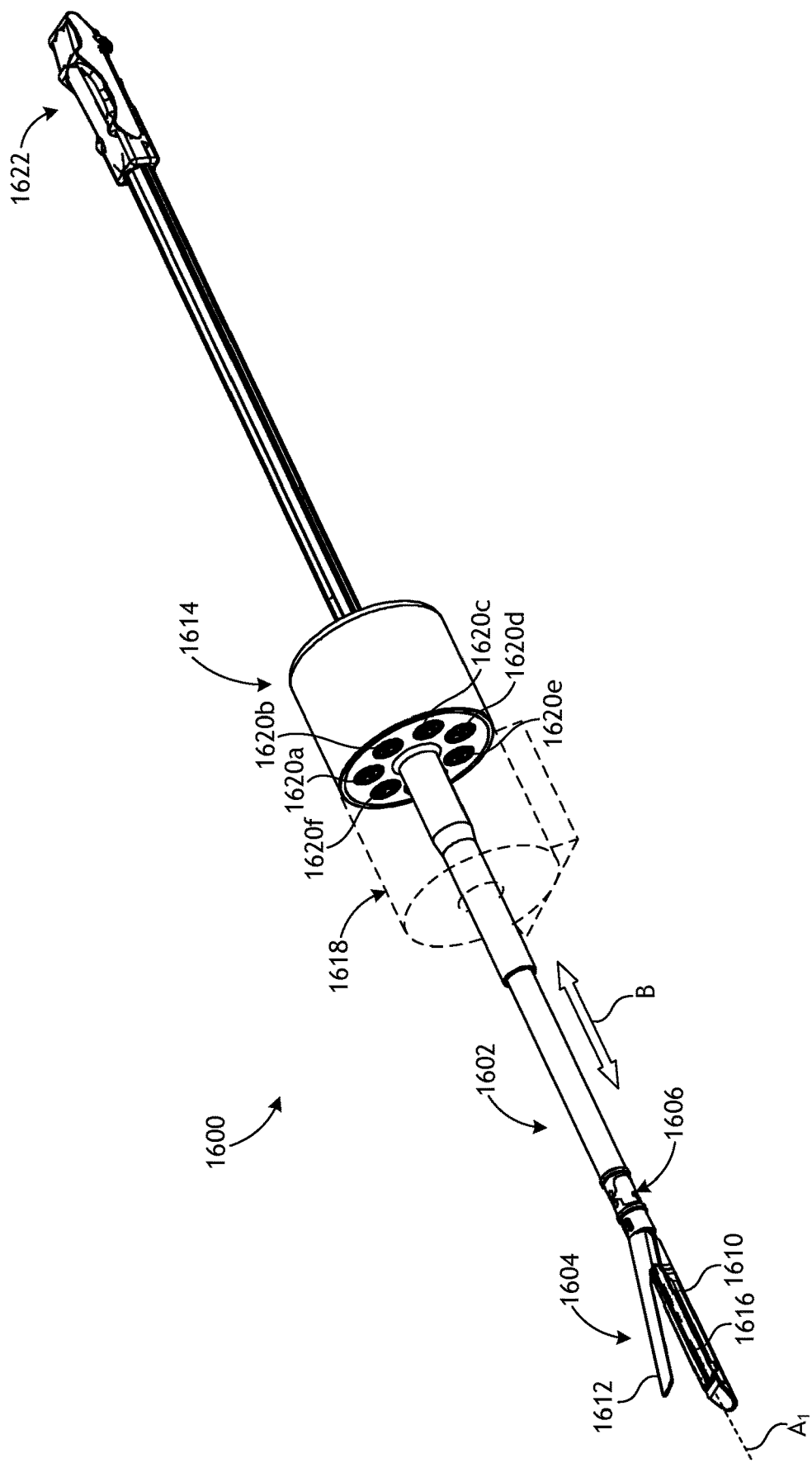
FIG. 16 is an isometric side view of an example surgical tool that may incorporate some or all of the principles of the present disclosure.

Embodiments of this disclosure relate to robotic surgical tools and accumulation systems that cause end effector operation. One robotic surgical tool includes a handle providing a drive input, an elongate shaft extendable through the handle and having an end effector arranged at a distal end of the shaft, an accumulator system housed within the handle and operatively coupled to the drive input such that actuation of the drive input operates the accumulator system, and at least one drive cable threaded through the accumulator system and extending distally along the shaft, wherein operation of the accumulator system alters at least one of a length or a force in the at least one drive cable to affect end effector operation FIG. 16 is an isometric side view of an example surgical tool 1600 that may incorporate some or all of the principles of the present disclosure. The surgical tool 1600 may be similar in some respects to any of the surgical tools and medical instruments described above with reference to FIGS. 11-13 and, therefore, may be used in conjunction with a robotic surgical system, such as the robotically-enabled systems 100, 400, and 900 of FIGS. 1-9C. As illustrated, the surgical tool 1600 includes an elongated shaft 1602, an end effector 1604 arranged at the distal end of the shaft 1602, and an articulable wrist 1606 (alternately referred to as a "wrist joint") that interposes and couples the end effector 1604 to the distal end of the shaft 1602. In some embodiments, the wrist 1606 may be omitted, without departing from the scope of the disclosure.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a surgical stapler, alternately referred to as an "endocutter," configured to cut and staple (fasten) tissue. As illustrated, the end effector 1604 includes opposing jaws 1610, 1612 configured to move (articulate) between open and closed positions. Alternatively, the end effector 1604 may comprise other types of instruments with opposing jaws such as, but not limited to, other types of surgical staplers (e.g., circular and linear staplers), tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In other embodiments, the end effector 1604 may instead comprise any end effector or instrument capable of being operated in conjunction with the presently disclosed robotic surgical systems and methods, such as a suction irrigator, an endoscope (e.g., a camera), or any combination thereof.

One or both of the jaws 1610, 1612 may be configured to pivot to actuate the end effector 1604 between open and closed positions. In the illustrated example, the second jaw 1612 may be rotatable (pivotable) relative to the first jaw 1610 to actuate the end effector 1604 between an open, unclamped position and a closed, clamped position. In other embodiments, however, the first jaw 1610 may move (rotate) relative to the second jaw 1612 to move the jaws 1610, 1612 between open and closed positions. In yet other embodiments, as discussed in more detail below, both jaws 1610, 1612 may simultaneously move (e.g., bifurcating jaws) to move the jaws 1610, 1612 between open and closed positions.

In the illustrated example, the first jaw 1610 is referred to as a "cartridge" or "channel" jaw, and the second jaw 1612 is referred to as an "anvil" jaw. The first jaw 1610 includes a frame that houses or supports a staple cartridge, and the second jaw 1612 is pivotally supported relative to the first jaw 1610 and defines a surface that operates as an anvil to deform staples ejected from the staple cartridge during operation.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis $A_1$ of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The end effector 1604 is depicted in FIG. 16 in the unarticulated position where the longitudinal axis of the end effector 1604 is substantially aligned with the longitudinal axis $A_1$ of the shaft 1602, such that the end effector 1604 is at a substantially zero angle relative to the shaft 1602. In the articulated position, the longitudinal axis of the end effector 1604 would be angularly offset from the longitudinal axis $A_1$ such that the end effector 1604 would be oriented at a non-zero angle relative to the shaft 1602.

Still referring to FIG. 16, the surgical tool 1600 may include a drive housing or "handle" 1614, and the shaft 1602 extends longitudinally through the handle 1614. The handle 1614 houses an actuation system designed to move the shaft 1602 relative to the handle 1614 (i.e., z-axis translation). Other actuation systems housed within the handle 1614, alternately referred to herein as "accumulator" systems, may be designed to facilitate articulation of the wrist 1606 and actuation (operation) of the end effector 1604 (e.g., clamping, firing, rotation, articulation, energy delivery, etc.). The actuation systems and mechanisms housed within the handle 1614 are actuatable to move (translate) a plurality of drive members (mostly obscured in FIG. 16) that extend along at least a portion of the shaft 1602, either on the exterior or within the interior of the shaft 1602. Example drive members include, but are not limited to, cables, bands, lines, cords, wires, woven wires, ropes, strings, twisted strings, elongate members, belts, shafts, flexible shafts, drive rods, or any combination thereof. The drive members can be made from a variety of materials including, but not limited to, a metal (e.g., tungsten, stainless steel, nitinol, etc.) a polymer (e.g., ultra-high molecular weight polyethylene), a synthetic fiber (e.g., KEVLAR®, VECTRAN®, etc.), an elastomer, or any combination thereof.

Selective actuation of one or more of the drive members, for example, may cause the shaft 1602 to translate relative to the handle 1614, as indicated by the arrows B (i.e., z-axis translation), and thereby advance or retract the end effector 1602. Selective actuation of one or more other drive members may cause the end effector 1604 to articulate (pivot) relative to the shaft 1602 at the wrist 1606. Selective actuation of one or more additional drive members may cause the end effector 1604 to actuate (operate). Actuating the end effector 1604 depicted in FIG. 16 may entail closing and/or opening the jaws, 1610, 1612 and thereby enabling the end effector 1604 to grasp (clamp) onto tissue. Once tissue is grasped or clamped between the opposing jaws 1610, 1612, actuating the end effector 1604 may further include "firing" the end effector 1604, which may refer to causing a cutting element or knife (not visible) to advance distally within a slot or "guide track" 1616 defined in the first jaw 1610. As it moves distally, the knife transects any tissue grasped between the opposing jaws 1610, 1612. Moreover, as the knife advances distally, a plurality of staples contained within the staple cartridge (e.g., housed within the first jaw 1610) are urged (cammed) into deforming contact with corresponding anvil surfaces (e.g., pockets) provided on the second jaw 1612. The deployed staples may form multiple rows of staples that seal opposing sides of the transected tissue.

As will be appreciated, however, the end effector 1604 may be replaced with any of the other types of end effectors mentioned herein, and in those cases actuating the end effector 1604 may entail a variety of other actions or movements, without departing from the scope of the disclosure. For example, in some embodiments, the end effector 1604 may be replaced with a vessel sealer and actuating such an end effector 1604 may further entail triggering energy delivery (e.g., RF energy) to cauterize and/or seal tissue or vessels.

The handle 1614 provides or otherwise includes various coupling features that releasably couple the surgical tool 1600 to an instrument driver 1618 (shown in dashed lines) of a robotic surgical system. The instrument driver 1618 may be similar in some respects to the instrument drivers 1102, 1200 of FIGS. 11 and 12, respectively, and therefore may be best understood with reference thereto. Similar to the instrument drivers 1102, 1200, for example, the instrument driver 1618 may be mounted to or otherwise positioned at the end of a robotic arm (not shown) and is designed to provide the motive forces required to operate the surgical tool 1600. Unlike the instrument drivers 1102, 1200, however, the shaft 1602 of the surgical tool 1600 extends through and penetrates the instrument driver 1618.

The handle 1614 includes one or more rotatable drive inputs matable with one or more corresponding drive outputs (not shown) of the instrument driver 1618. Each drive input is actuatable to independently drive (actuate) the actuation (accumulation) systems and mechanisms housed within the handle 1614 and thereby operate the surgical tool 1600. In the illustrated embodiment, the handle 1614 includes a first drive input 1620a, a second drive input 1620b, a third drive input 1620c, a fourth drive input 1620d, a fifth drive input 1620e, and a sixth drive input 1620f. While six drive inputs 1620a-f are depicted, more or less than six may be included in the handle 1614 depending on the application, and without departing from the scope of the disclosure. Each drive input 1620a-f may be matable with a corresponding drive output (not shown) of the instrument driver 1618 such that movement (rotation) of a given drive output correspondingly moves (rotates) the associated drive input 1620a-f and thereby causes various operations of the surgical tool 1600.

In some embodiments, actuation of the first drive input 1620a may cause the knife to fire at the end effector 1604, thus advancing or retracting the knife, depending on the rotational direction of the first drive input 1620a. Actuation of the third drive input 1620c may cause the shaft 1602 to move (translate) relative to the handle 1614 along the longitudinal axis $A_1$, depending on the rotational direction of the third drive input 1620c. In some embodiments, actuation of the second drive input 1620b may shift operation or activation within the handle 1614 between the first and third drive inputs 1620a,c. Consequently, actuation of the second drive input 1620b will dictate whether the knife is fired or whether the shaft 1602 is moved (translated). Actuation of the fourth drive input 1620d may lock and unlock z-axis translation of the shaft 1602, and actuation of the fifth drive input 1620e may cause articulation of the end effector 1604 at the wrist 1606. Lastly, actuation of the sixth drive input 1620f may cause the jaws 1610, 1612 to open or close, depending on the rotational direction of the sixth drive input 1620f. In some embodiments, actuation of the sixth drive input 1620f may operate a toggle mechanism 1622 arranged at the proximal end of the shaft 1602, and actuation of the toggle mechanism 1622 may cause the jaws 1610, 1612 to open and close.

Figure 17:
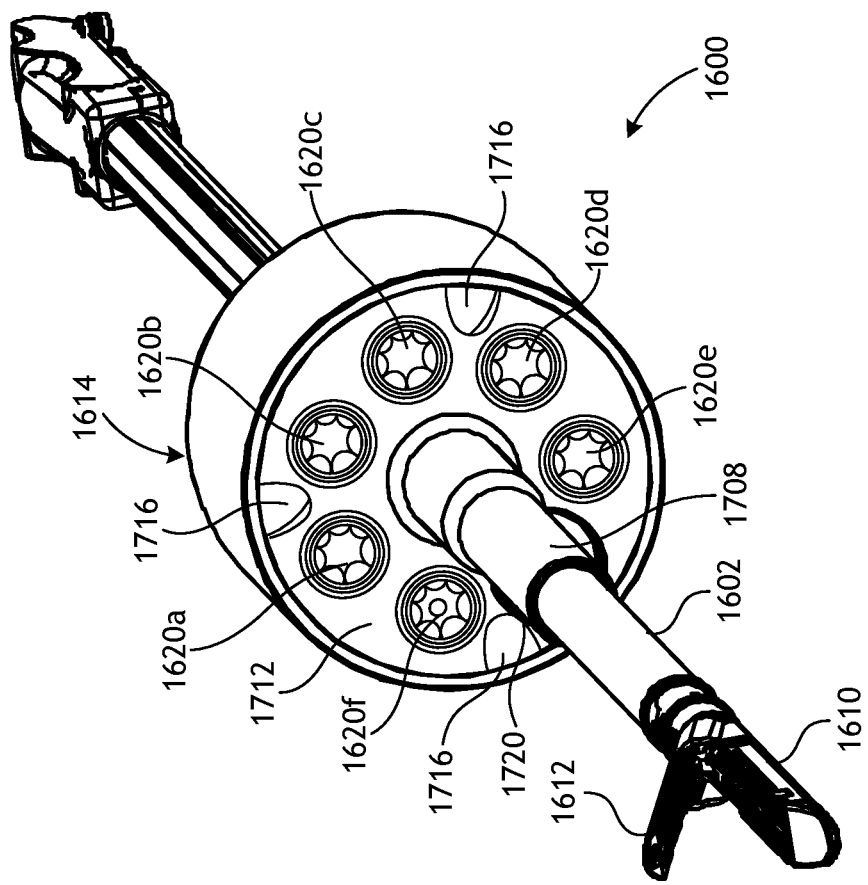
FIG. 17 depicts separated isometric end views of the instrument driver and the surgical tool of FIG. 16.
Figure 17:
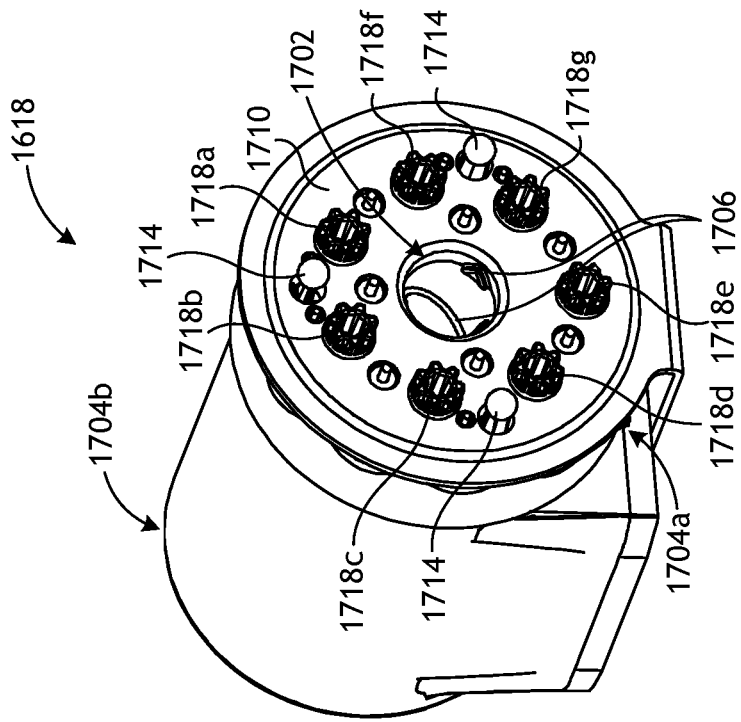

FIG. 17 depicts separated isometric end views of the instrument driver 1618 and the surgical tool 1600 of FIG. 16. With the jaws 1610, 1612 closed, the shaft 1602 and the end effector 1604 can penetrate the instrument driver 1618 by extending through a central aperture 1702 defined longitudinally through the instrument driver 1618 between first and second ends 1704a,b. In some embodiments, to align the surgical tool 1600 with the instrument driver 1618 in a proper angular orientation, one or more alignment guides 1706 may be provided or otherwise defined within the central aperture 1702 and configured to engage one or more corresponding alignment features (not shown) provided on the surgical tool 1600. The alignment feature(s) may comprise, for example, a protrusion or projection (not shown) defined on or otherwise provided by an alignment nozzle 1708 extending distally from the handle 1614. In one or more embodiments, the alignment guide(s) 1706 may comprise a curved or arcuate shoulder or lip configured to receive and guide the alignment feature as the alignment nozzle 1708 enters the central aperture 1702. As a result, the surgical tool 1600 is oriented to a proper angular alignment with the instrument driver 1618 as the alignment nozzle 1708 is advanced distally through the central aperture 1702. In other embodiments, the alignment nozzle 1708 may be omitted and the alignment feature 1712 may alternatively be provided on the shaft 1602, without departing from the scope of the disclosure.

A drive interface 1710 is provided at the first end 1704a of the instrument driver 1618 and is matable with a driven interface 1712 provided on the distal end of the handle 1614. The drive and driven interfaces 1710, 1712 may be configured to mechanically, magnetically, and/or electrically couple the handle 1614 to the instrument driver 1618. To accomplish this, in some embodiments, the drive and driven interfaces 1710, 1712 may provide one or more matable locating features configured to secure the handle 1614 to the instrument driver 1618. In the illustrated embodiment, for example, the drive interface 1710 provides one or more interlocking features 1714 (three shown) configured to locate and mate with one or more complementary-shaped pockets 1716 (two shown, one occluded) provided on the driven interface 1712. In some embodiments, the features 1714 may be configured to align and mate with the pockets 1716 via an interference or snap fit engagement, for example.

The instrument driver 1618 also includes one or more drive outputs that extend through the drive interface 1710 to mate with corresponding drive inputs 1620a-f provided at the distal end of the handle 1614. More specifically, the instrument driver 1618 includes a first drive output 1718a matable with the first drive input 1620a, a second drive output 1718b matable with the second drive input 1620b, a third drive output 1718b matable with the third drive input 1620c, a fourth drive output 1718d matable with the fourth drive input 1620d, a fifth drive output 1718e matable with the fifth drive input 1620e, and a sixth drive output 1718f matable with the sixth drive input 1620f. In some embodiments, as illustrated, the drive outputs 1718a-f may define splines or features designed to mate with corresponding splined receptacles of the drive inputs 1620a-f. Once properly mated, the drive inputs 1620a-f will share axes of rotation with the corresponding drive outputs 1718a-f to allow the transfer of rotational torque from the drive outputs 1718a-f to the corresponding drive inputs 1620a-f. In some embodiments, each drive output 1718a-f may be spring loaded and otherwise biased to spring outwards away from the drive interface 1710. Each drive output 1718a-f may be capable of partially or fully retracting into the drive interface 1710.

In some embodiments, the instrument driver 1618 may include additional drive outputs, depicted in FIG. 17 as a seventh drive output 1718g. The seventh drive output 1718g may be configured to mate with additional drive inputs (not shown) of the handle 1614 to help undertake one or more additional functions of the surgical tool 1600. In the illustrated embodiment, however, the handle 1614 does not include additional drive inputs matable with the seventh drive output 1718g. Instead, the driven interface 1712 defines a corresponding recess 1720 (partially occluded) configured to receive the seventh drive output 1718g. In other applications, however, a seventh drive input (not shown) could be included in the handle 1614 to mate with the seventh drive output 1718g, or the surgical tool 1600 might be replaced with another surgical tool having a seventh drive input, which would be driven by the seventh drive output 1718g.

While not shown, in some embodiments, an instrument sterile adapter (ISA) may be placed at the interface between the instrument driver 1618 and the handle 1614. In such applications, the interlocking features 1714 may operate as alignment features and possible latches for the ISA to be placed, stabilized, and secured. Stability of the ISA may be accomplished by a nose cone feature provided by the ISA and extending into the central aperture 1702 of the instrument driver 1618. Latching can occur either with the interlocking features 1714 or at other locations at the interface. In some cases, the ISA will provide the means to help align and facilitate the latching of the surgical tool 1600 to the ISA and simultaneously to the instrument driver 1618.

Lead Screw & Plate Accumulator for Dual Cable Drive

Figure 18:
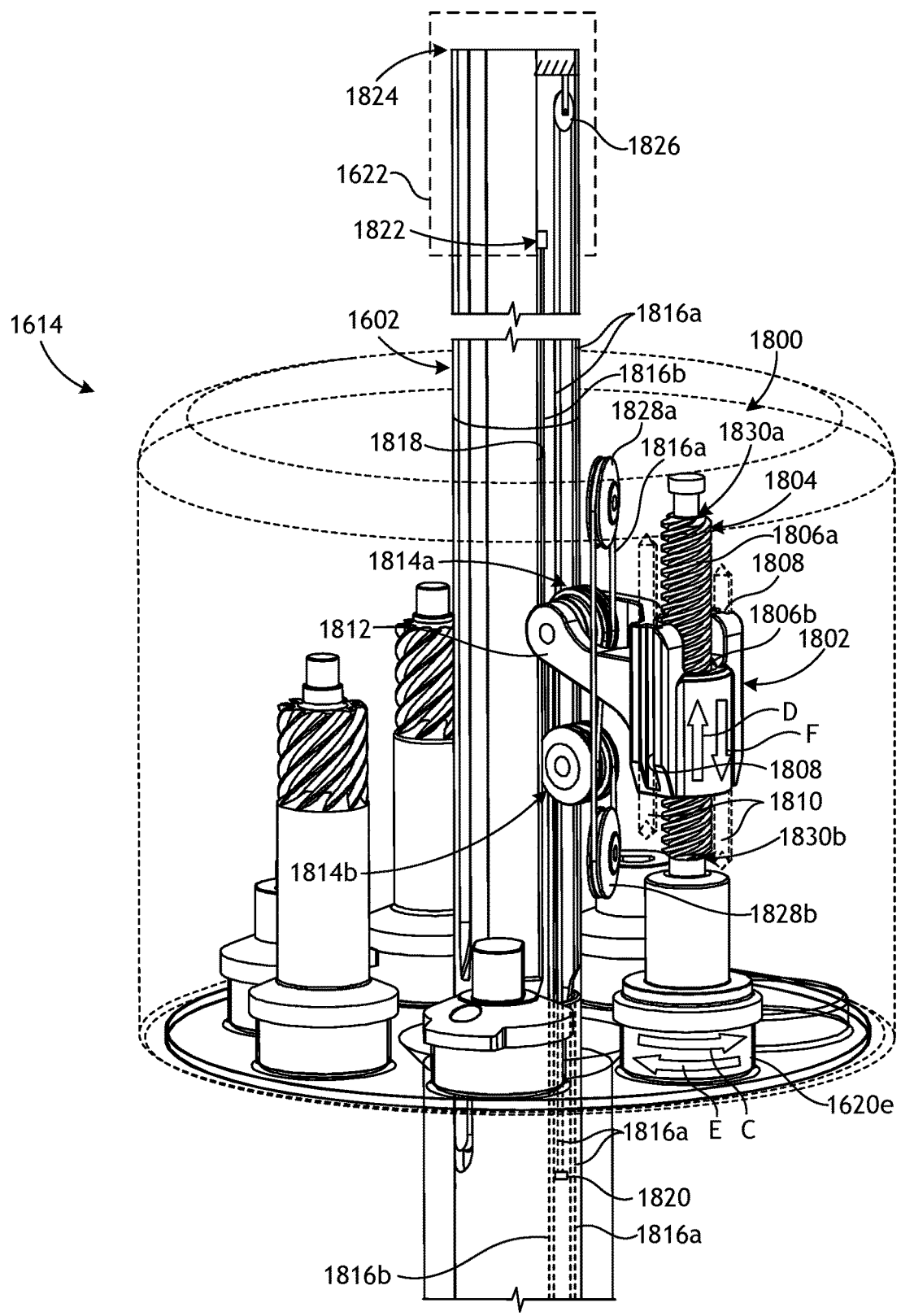
FIG. 18 is an enlarged isometric view of the handle of FIGS. 16-17 depicting an example accumulator system, according to one or more embodiments.

FIG. 18 is an enlarged isometric view of the handle 1614 depicting an example accumulator system 1800, according to one or more embodiments. The outer body of the handle 1614 is shown in phantom (dashed lines) to enable viewing of the internal space within the handle 1614, including the accumulator system 1800 (alternately referred to as an "actuation" system). Various other accumulator systems and component parts of the handle 1614 are omitted in FIG. 18 for simplicity.

The accumulator system 1800 may be operable (actuatable) to carry out a variety of functions (operations) of the surgical tool 1600 (FIG. 16). In some embodiments, for example, operation of the accumulator system 1800 may cause the end effector 1604 (FIG. 16) to articulate at the wrist 1606 (FIGS. 16-17). In such embodiments, the accumulator system 1800 may include or otherwise be operatively coupled to the fifth drive input 1620e, and rotation (actuation) of the fifth drive input 1620e, via operation of the fifth drive output 1718e (FIG. 17), may cause the accumulator system 1800 to operate and cause articulation of the end effector 1604.

In other embodiments, however, the accumulator system 1800 may be operable to cause the end effector 1604 (FIG. 16) to "fire," as generally described above. In such embodiments, the accumulator system 1800 may be operatively coupled to the first drive input 1620a (FIGS. 16-17), and rotation (actuation) of the first drive input 1620a, via operation of the first drive output 1718a (FIG. 17), may cause the accumulator system 1800 to operate and cause a knife arranged at the end effector 1604 to advance or retract, depending on the rotational direction of the first drive input 1620a. In yet other embodiments, however, the accumulator system 1800 may be designed to carry out other functions (operations) of the surgical tool 1600 (FIG. 16), such as causing the shaft 1602 (FIGS. 16-17) to translate relative to the handle 1614, or opening or closing the jaws 1610, 1612 (FIGS. 16-17) at the end effector 1604, without departing from the scope of the disclosure.

In the illustrated embodiment, the accumulator system 1800 includes a nut 1802 coupled to a lead screw 1804 extending from the fifth drive input 1620e. The lead screw 1804 may be coupled to or form part of the fifth drive input 1620e such that rotation of the fifth drive input 1620e correspondingly rotates the lead screw 1804 in the same direction. Moreover, the lead screw 1804 defines external helical threading 1806a matable with internal helical threading 1806b defined by the nut 1802. Consequently, as the lead screw 1804 rotates, threaded engagement between the external and internal threading 1806a,b urges the nut 1802 to traverse the lead screw 1804 either proximally or distally (e.g., up or down the lead screw 1804), depending on the rotation direction of the lead screw 1804. In some embodiments, the internal threading 1806b may be defined on a portion of the nut 1802 itself, but in other embodiments the internal threading 1806b may be defined on a linear slide element (not shown) disposed within or otherwise coupled to the nut 1802.

In some embodiments, the nut 1802 may provide one or more channel guides 1808 (two shown) configured to receive opposing guide structures 1810 (shown in phantom dashed lines) provided by the handle 1614 or otherwise operatively coupled thereto. As the nut 1802 traverses the length of the lead screw 1804, the guide structures 1810 slide within the channel guides 1808 to provide support and thereby help prevent the nut 1802 from rotating as the lead screw 1804 rotates.

The nut 1802 may provide or otherwise include an armature 1812 extending laterally from the nut 1802 and toward the shaft 1602. In some embodiments, a first or "upper" pulley 1814*a* may be rotatably mounted to the armature 1812, such as at or near the end of the armature 1812. A second or "lower" pulley 1814*b* may be rotatably coupled to the handle 1614 and axially offset from the upper pulley 1814*a*. Accordingly, movement of the nut 1802 along the lead screw 1804 will correspondingly move the upper pulley 1814*a* toward or away from the lower pulley 1814*b*, which remains stationary relative to the handle 1614 during operation. In some embodiments, as illustrated, the pulleys 1814*a,b* may comprise double barrel pulleys (alternately referred to as "double pulleys") capable of accommodating two or more drive members or drive cables.

The accumulator system 1800 may further include a first drive member 1816*a* and a second drive member 1816*b* that extend longitudinally along at least a portion of the shaft 1602 and interact with the pulleys 1814*a,b*. In the illustrated embodiment, each drive member 1816*a,b* comprises a cable or wire and, therefore, will be referred to herein as "drive cables 1816*a,b*". In other embodiments, however, the drive cables 1816*a,b* may comprise any of the other types of drive members mentioned herein and may thus alternatively comprise a band, a line, a cord, a wire, a woven wire, a rope, a string, a twisted string, an elongate member, a belt, a flexible shaft, or any combination thereof. Moreover the drive cables 1816*a,b* can be made from a variety of materials including, but not limited to, a metal (e.g., tungsten, stainless steel, nitinol, etc.), a metallic braided cable, a polymer (e.g., ultra-high molecular weight polyethylene or Dyneema®), a polymer braided cable, a synthetic fiber (e.g., KEVLAR®, VECTRAN®, etc.), an elastomer, or any combination thereof.

In some embodiments, the drive cables 1816*a,b* may extend along the shaft 1602 within a groove 1818 defined in the shaft 1602. In other embodiments, however, the drive cables 1816*a,b* may alternatively be received within the interior of the shaft 1602 or extend along an exterior surface of the shaft 1602, without departing from the scope of the disclosure.

In some embodiments, a first end 1820 of the first drive cable 1816*a* may be anchored to the shaft 1602 below (distal to) the handle 1614, and a first end 1822 of the second drive cable 1816*b* may be anchored to the shaft 1602 above (proximal to) the handle 1614. As will be appreciated, the drive cables 1816*a,b* may be anchored to the shaft 1602 distal and proximal to the handle 1614 at sufficient distance to allow the shaft 1602 to be able to travel through handle 1614 in z-axis translation. Moreover, the first drive cable 1816*a* may extend proximally toward a proximal end 1824 of the shaft 1602 where it may be looped around a shaft pulley 1826 and extend back down the shaft 1602 toward its distal end. The shaft pulley 1826 may be fixed at or near the proximal end 1824 of the shaft 1602. In at least one embodiment, the shaft pulley 1826 may be coupled to or form part of the toggle mechanism 1622 (generally depicted as a dashed box) or a tailpiece operatively coupled at or near the proximal end 1824. As discussed in more detail below, the second ends of each drive cable 1816*a,b* may extend distally along the shaft 1602 to the end effector 1604 (FIG. 16) and/or the wrist 1606 (FIGS. 16-17) and may help facilitate one or more functions of the end effector 1604 or the wrist 1606, such as causing the end effector 1604 to articulate or fire.

The accumulator system 1800 may further include a first or "upper" idler pulley 1828*a* and a second or "lower" idler pulley 1828*b*. The upper and lower idler pulleys 1828*a,b* may each be rotatably coupled to the handle 1614 and longitudinally (axially, vertically, etc.) offset from each other. More specifically, in some embodiments, the upper idler pulley 1828*a* may be mounted within the handle 1614 at or above a proximal end 1830*a* of the external threading 1806*a*, and the lower idler pulley 1828*b* may be mounted within the handle 1614 at or below a distal end 1830*b* of the external threading 1806*a*. Consequently, movement of the nut 2102 along the lead screw 2104 may not be able to surpass the position of the idler pulleys 1828*a,b* on either end 1830*a,b* of the lead screw 2104.

In some embodiments, the pulleys 1814*a,b* may have parallel axes of rotation, and the idler pulleys 1828*a,b* may have parallel axes of rotation. In at least one embodiment, the axes of rotation of the pulleys 1814*a,b* and the idler pulleys 1828*a,b* may be parallel, but may alternatively be non-parallel, as illustrated. Moreover, in some embodiments, the pulleys 1814*a,b* may be arranged for rotation in a same plane, and the idler pulleys 1828*a,b* may be arranged for rotation in a same plane, but the idler pulleys 1828*a,b* may alternatively be arranged for rotation in separate planes. As illustrated, the idler pulleys 1828*a,b* may be arranged for rotation in a plane that is offset from the rotation plane of the pulleys 1814*a,b*, but could alternatively be arranged for rotation in the same plane as the pulleys 1814*a,b*, without departing from the scope of the disclosure.

As illustrated, the drive cables 1816*a,b* may extend or be threaded (guided) through the accumulator system 1800 and, more particularly, through the pulleys 1814*a,b* and the idler pulleys 1828*a,b* within the body of the handle 1614. The upper pulley 1814*a* may be arranged and otherwise configured to receive the first drive cable 1816*a* from a proximal portion of the shaft 1602 and redirect the first drive cable 1816*a* from the shaft 1602 to the upper idler pulley 1828*a*. The upper idler pulley 1828*a* may then redirect the first drive cable 1816*a* to the lower idler pulley 1828*b*, which may redirect the first drive cable 1816*a* to the lower pulley 1814*b*. The lower pulley 1814*b* may be arranged to redirect the first drive cable 1816*a* back to the shaft 1602 (e.g., within the groove 1818) to extend distally along the shaft 1602 until the first end 1820 is anchored to the shaft 1602. In contrast, the lower pulley 1814*b* may be arranged and otherwise configured to receive the second drive cable 1816*b* from the proximal portion of the shaft 1602 where the first end 1822 of the second drive cable 1816*b* is anchored to the shaft 1602. The lower pulley 1814*b* may redirect the second drive cable 1816*b* from the shaft 1602 to the upper pulley 1814*a*, and the upper pulley 1814*a* may then redirect the second drive cable 1816*a* back to the shaft 1602 (e.g., within the groove 1818) to extend distally along the shaft 1602.

As mentioned above, the accumulator system 1800 may be actuated or operated by rotating the fifth drive input 1620*e*, via operation of the fifth drive output 1718*e* (FIG. 17). Rotating the fifth drive input 1620*e* in a first angular direction C (e.g., clockwise) will correspondingly rotate the lead screw 1804 in the same direction C and thereby cause the nut 1802 to move proximally along the lead screw 1804, as indicated by the arrow D. Moving the nut 1802 proximally D simultaneously moves the upper pulley 1814*a* away from the lower pulley 1814*b*. In contrast, rotating the fifth drive input 1620*e* in a second angular direction E (e.g., counter-clockwise) opposite the first angular direction C will correspondingly rotate the lead screw 1804 in the same direction E and thereby cause the nut 1802 to move distally along the lead screw 1804, as indicated by the arrow F. Moving the nut 1802 distally F simultaneously moves the upper pulley 1814*a* toward the lower pulley 1814*b*.

Actuation or operation of the accumulator system 1800 may result in antagonistic manipulation of the drive cables 1816*a,b*, which can help facilitate one or more functions of the end effector 1604 (FIG. 16) or the wrist 1606 (FIGS. 16-17), such as causing the end effector 1604 to articulate or causing the end effector 1604 to fire. More specifically, movement of the nut 1802 along the lead screw 1804 may result in the overall lengths of the drive cables 1816*a,b* changing along the shaft 1602 equally and opposite by a factor of two times (2×) the motion of the nut 1802. This is possible since the first ends 1820, 1822 of the drive cables 1816*a,b* are each fixed at opposite ends of the shaft 1602 and guided through (nested within) the upper and lower pulleys 1814*a,b*, where the upper pulley 1814*a* is able to move toward or away from the lower pulley 1814*b* based on rotational direction of the lead screw 1804.

In example operation, as the nut 1802 is actuated to move proximally D along the lead screw 1804 by one (1) unit of length, the accumulator system 1800 will pay out (dispense) two (2) units of length of the first drive cable 1816*a* to the shaft 1602, and thereby remove tension from or slacken the first drive cable 1816*a*, and simultaneously pay in (draw in) two (2) units of length of the second drive cable 1816*b* from the shaft 1602, and thereby increase tension in the second drive cable 1816*b*. In contrast, as the nut 1802 is actuated to move distally F along the lead screw 1804 by one (1) unit of length, the accumulator system 1800 will pay in (draw in) two (2) units of length of the first drive cable 1816*a* from the shaft 1602, and thereby increase tension in the first drive cable 1816*a*, and simultaneously pay out (dispense) two (2) units of length of the second drive cable 1816*b* to the shaft 1602, and thereby remove tension from or slacken the first drive cable 1816*a*. Such antagonistic and simultaneous operation of the drive cables 1816*a,b* can help operate the end effector 1604 (FIG. 16) or the wrist 1606 (FIGS. 16-17), as discussed below.

While depicted in FIG. 18 as floating (unsupported), lower pulley 1814*b* and the idler pulleys 1828*a,b* will be rotatably coupled to various structural elements or stationary features of the handle 1614 not shown in FIG. 18. Moreover, in some embodiments, the accumulator system 1800 may be decoupled from shaft 1602 insertion relative to the handle 1614. More specifically, the pulleys 1814*a,b*, the idler pulleys 1828*a,b*, and the shaft pulley 1826 may be able to freely rotate (e.g., "free wheel") and are otherwise not driven during operation of the handle 1614. Consequently, as the shaft 1602 moves longitudinally relative to the handle 1614 in z-axis translation, the drive cables 1816*a,b* are able to freely run (course) through the pulleys 1814*a,b*, the idler pulleys 1828*a,b*, and the shaft pulley 1826. Moreover, since the pulleys 1814*a,b*, the idler pulleys 1828*a,b*, and the shaft pulley 1826 are able to freely rotate, the accumulator system 1800 can be operated simultaneously during shaft 1602 z-axis translation relative to the handle 1614.

Figure 19:
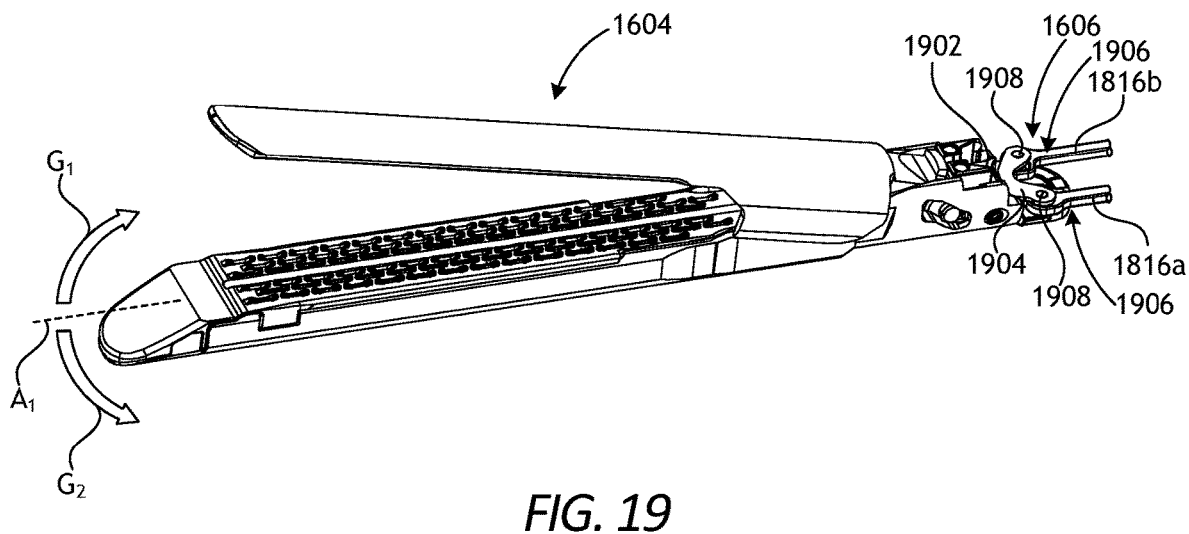
FIG. 19 is an enlarged isometric view of the end effector and an exposed view of the wrist of FIGS. 16-17, according to one or more embodiments.

Referring now to FIG. 19, with continued reference to FIG. 18, depicted is an enlarged isometric view of the end effector 1604 and an exposed view of a portion of the wrist 1606, according to one or more embodiments. In FIG. 19, the shaft 1602 (FIG. 18) has been removed to enable viewing of the operative connection between the drive cables 1816*a,b* and the wrist 1606. In some embodiments, as mentioned above, the accumulator system 1800 (FIG. 18) may be operable to cause the end effector 1604 to articulate at the wrist 1606. More specifically, the accumulator system 1800 may cause antagonistic pull-pull translation of the drive cables 1816, which acts on the wrist 1606 to cause the end effector 1604 to pivot either clockwise, as indicated by the arrow $G_1$, or counter-clockwise, as indicated by the arrow $G_2$.

In the illustrated embodiment, the end effector 1604 is mounted to an end effector mount 1902 that includes a distal link 1904 coupled to or otherwise extending from the end effector mount 1902. The end effector mount 1902 and the distal link 1904 together comprise a linkage configured to help articulate end effector mount 1902, and therefore the end effector 1604, in a plane parallel to the longitudinal axis $A_1$.

The drive cables 1816*a,b* may extend to the wrist 1606 and may be operatively coupled to the distal link 1904. In some embodiments, for example, a distal end 1906 of each drive cable 1816*a,b* may be coupled to the distal link 1904 at corresponding articulation pins 1908. As the first drive cable 1816*a* is pulled proximally, as actuated by the accumulator system 1800 (FIG. 18), the second drive cable 1816*b* will be drawn distally, and as the second drive cable 1816*b* is pulled proximally, as actuated by the accumulator system 1800, the first drive cable 1816*a* will be moved (drawn) distally. The pull-pull antagonistic operation of the drive cables 1816*a,b* cooperatively acts on the end effector mount 1902 via the distal link 1904 to cause the end effector 1604 to rotate either clockwise $G_1$ or counter-clockwise $G_2$.

Figure 20:
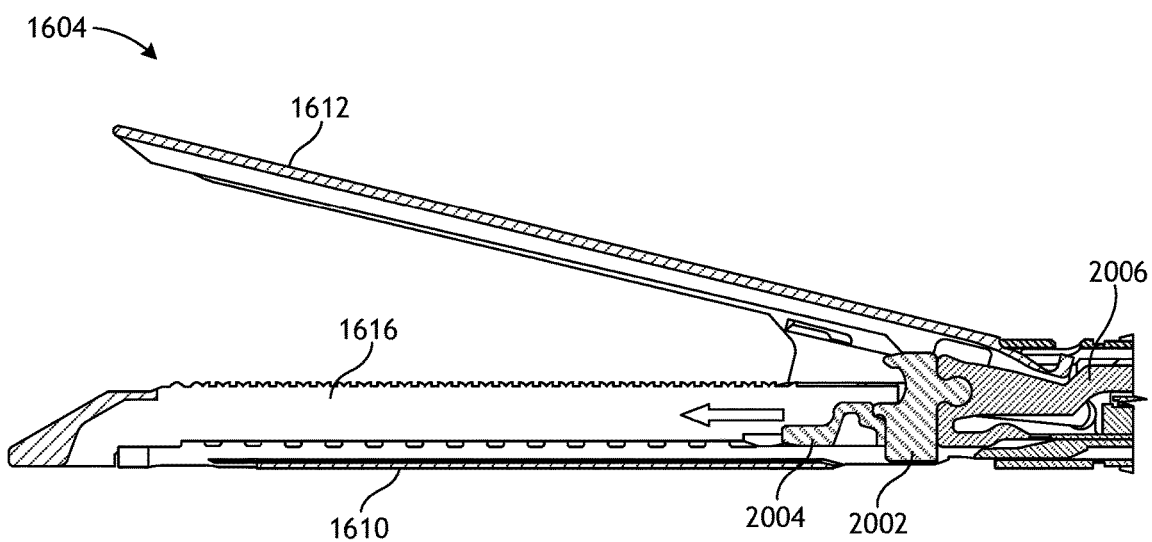
FIG. 20 is an enlarged cross-sectional view of the end effector of FIGS. 16-17, according to one or more embodiments.

Referring now to FIG. 20, with continued reference to FIG. 18, depicted is an enlarged cross-sectional view of the end effector 1604, according to one or more embodiments. In some embodiments, as mentioned above, the accumulator system 1800 (FIG. 18) may be operable to cause the end effector 1604 to "fire," as generally described above. More specifically, the end effector 1604 may include a knife 2002, and operation of the accumulator system 1800 may cause the knife 2002 to be linearly displaced within the guide track 1616 to cut tissue grasped between the jaws 1610, 1612. In embodiments where the end effector 1604 comprises a surgical stapler, distally advancing the knife 2002 within the guide track 1616 may simultaneously advance a sled or camming wedge 2004, which engages a plurality of staples (not shown) contained within the lower jaw 1610 (e.g., within a staple cartridge) and urges (cams) the staples into deforming contact with the opposing anvil surfaces (e.g., pockets) provided on the upper jaw 1612. Properly deployed staples help seal opposing sides of the transected tissue.

As illustrated, the knife 2002 may be operatively coupled to a firing rod 2006 coupled to and extend proximally (i.e., to the right in FIG. 20) from the knife 2002. The firing rod 2006 forms part of a knife drive system, and actuating the firing rod 2106 causes the firing rod 2106 to linearly advance and retract and correspondingly advance and retract the knife 2002. In embodiments where the end effector 1604 comprises a surgical stapler, distal movement of the firing rod 2106 also correspondingly moves the camming wedge 2004 to deploy the staples.

Figure 21A:
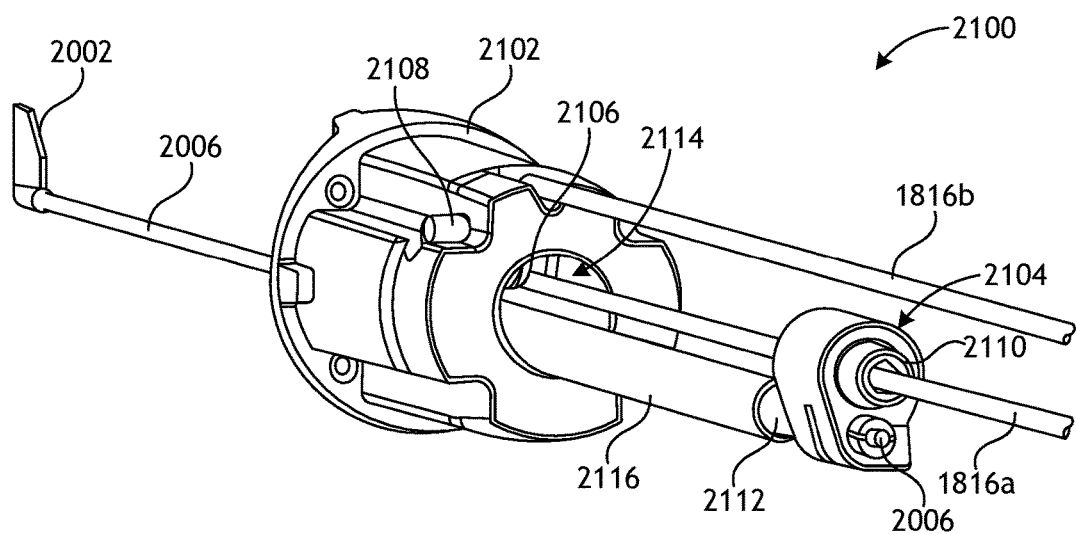
FIGS. 21A and 21B are back and front isometric views, respectively of an example knife drive system, according to one or more embodiments.
Figure 21B:
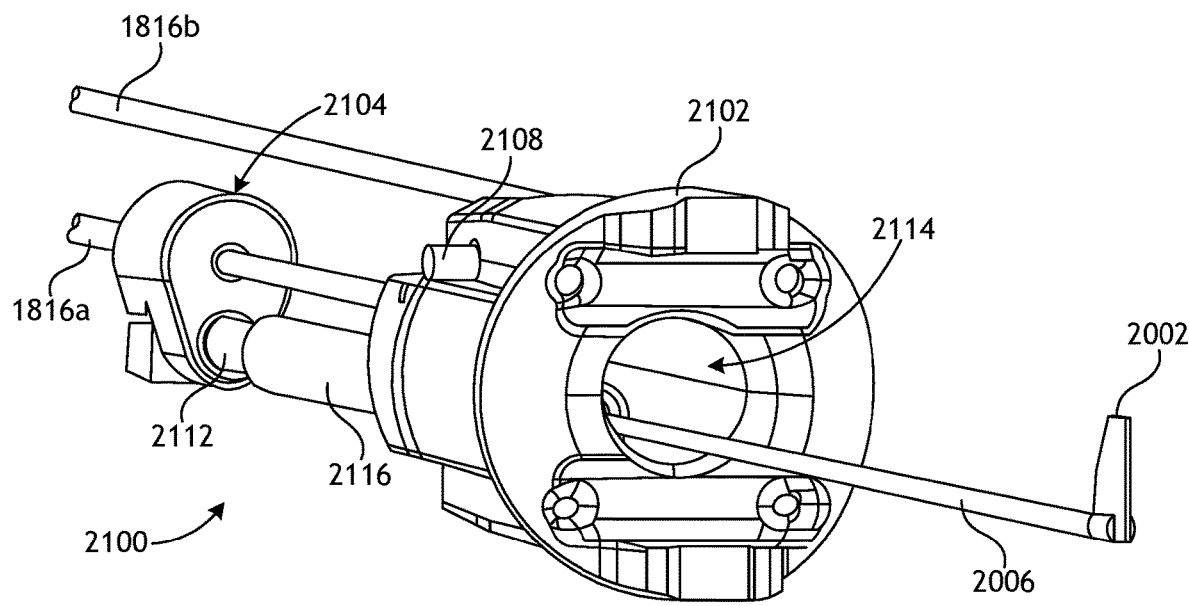

FIGS. 21A and 21B are isometric back and front views, respectively of an example cable-based knife drive system 2100, according to one or more embodiments. The knife drive system 2100 may be incorporated into the surgical tool 1600 of FIG. 16 to advance and retract the knife 2002 during operation. More specifically, the first and second drive cables 1816*a,b* may extend to the knife drive system 2100 such that operation of the accumulator system 1800 (FIG. 18) will antagonistically operate the drive cables 1816a,b and thereby cause the knife drive system 2100 to actuate and advance or retract the knife 2002.

As illustrated, the knife drive system 2100 may be mounted to a shaft adapter 2102 at or near the wrist 1606 (FIG. 16). In some embodiments, the shaft adapter 2102 may form an integral part or extension of the shaft 1602 (FIG. 16) or an interconnecting linkage between the shaft 1602 and the wrist 1606. In other embodiments, the shaft adapter 2102 may comprise an articulation joint of the wrist 1602, but may alternatively be pivotably coupled to the articulation joint, without departing from the scope of the disclosure.

As illustrated, the first drive cable 1816a is coupled to and terminates at a collar 2104, and the second drive cable 1816b loops around a pulley 2106 (FIG. 21A) and is also coupled to the collar 2104. The pulley 2106 is rotatably mounted to the shaft adapter 2102 at a pin 2108. In some embodiments, one or both of the drive cables 1816a,b may be crimped or knotted and the crimp or knot may be trapped between the collar 2104 and a stop member 2110 secured within the collar 2104.

A proximal end of the drive rod 2006 may also be coupled to the collar 2104 such that longitudinal movement of the collar 2104 correspondingly moves the drive rod 2006 in the same direction and thereby advances or retracts the knife 2002. In some embodiments, as illustrated, the drive rod 2006 may be received within a flexible tube 2112. The flexible tube 2112 may support the drive rod 2006 and help prevent buckling upon assuming compressive loads during articulation of the wrist 1606 and opening and closure of the jaws 1610, 1612 (FIGS. 16 and 20). The flexible tube 2112 may be made of a variety of flexible materials including, but not limited to, a metal or metal alloy (e.g., a nickel-titanium alloy or "nitinol"), a metallic coil, a plastic or thermoplastic material, a composite material, or any combination thereof.

The drive rod 2006 may extend through a central aperture 2114 defined longitudinally through the shaft adapter 2102. In some embodiments, a hypotube 2116 may surround the drive rod 2006 and the flexible member 2112 (or only the drive rod 2006) as extending through the central aperture 2114. During operation, the drive rod 2006 and the flexible member 2112 (or only the drive rod 2006) slide longitudinally through the hypotube 2116, and the hypotube 2116 may help to prevent buckling of the drive rod 2006.

In example operation, actuation of the drive cables 1816a,b, via operation of the accumulator system 1800 (FIG. 18), causes the drive rod 2006 and the knife 2002 to move distally or proximally as coupled to the collar 2104. More specifically, operating the accumulator system 1800 can pay in (draw in) a portion of the first drive cable 1816a and simultaneously pay out (dispense) a portion of the second drive cable 1816b. This results in tension (i.e., pull force) being applied on the first drive cable 1816a and slackening of the second drive cable 1816b. Tension on the first drive cable 1816a pulls the first drive cable 1816a proximally and simultaneously pulls (moves) the collar 2104 in the same direction. As the first drive cable 1816a moves proximally, the drive rod 2006 and the knife 2002 also move proximally as coupled to the collar 2104. Moreover, the slackened second drive cable 1816b is able to naturally follow movement of the first drive cable 1816a as coupled to the collar 2104.

Reversing operation of the accumulator system 1800 (FIG. 18) can pay in (draw in) a portion of the second drive cable 1816b and simultaneously pay out (dispense) a portion of the first drive cable 1816a. This results in tension (i.e., pull force) being applied on the second drive cable 1816b and simultaneous slackening of the first drive cable 1816a, which drives the collar 2104, the drive rod 2006, and the knife 2002 distally. Accordingly, antagonistic pull-pull operation of the drive cables 1816a,b advances or retracts the knife 2002, depending on the pull direction.

Accumulator Systems with Beveled Gear Assemblies

Figure 22A:
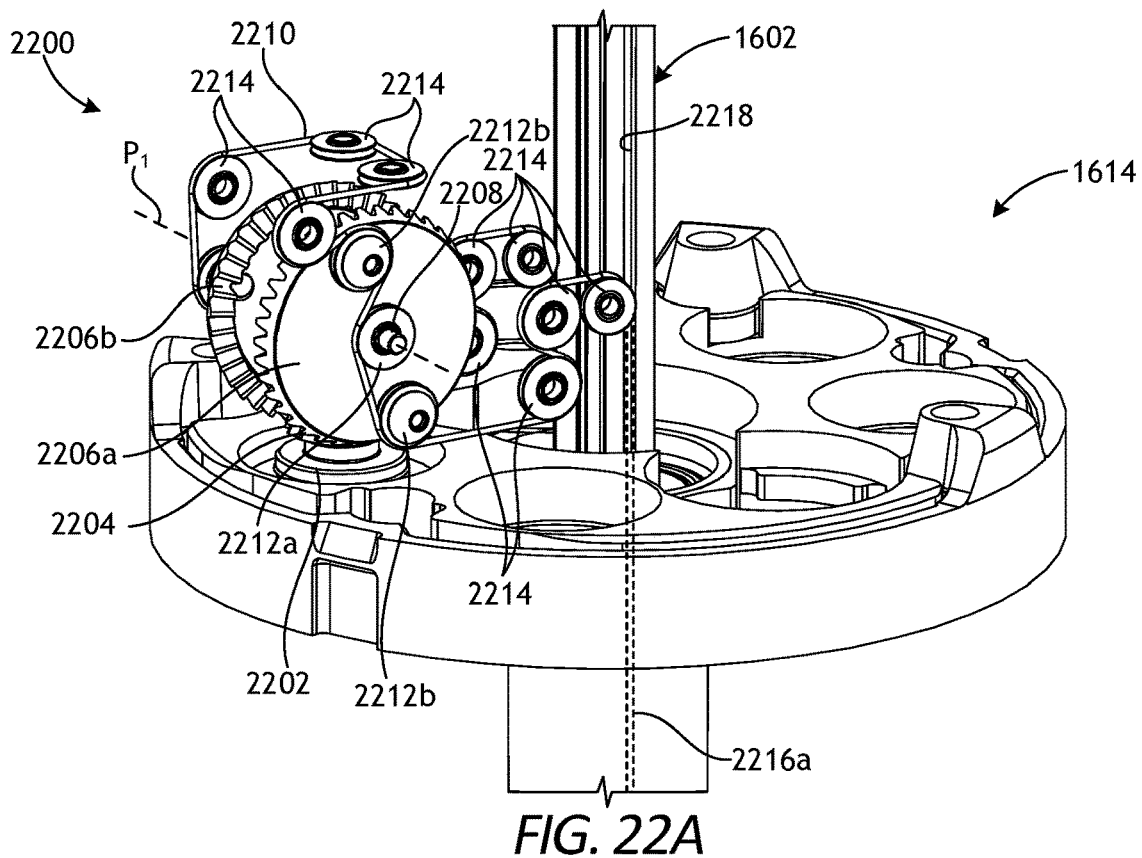
FIGS. 22A and 22B are opposing isometric side views of another example accumulator system that may be incorporated into the handle of FIGS. 16-17, according to one or more additional embodiments.
Figure 22B:
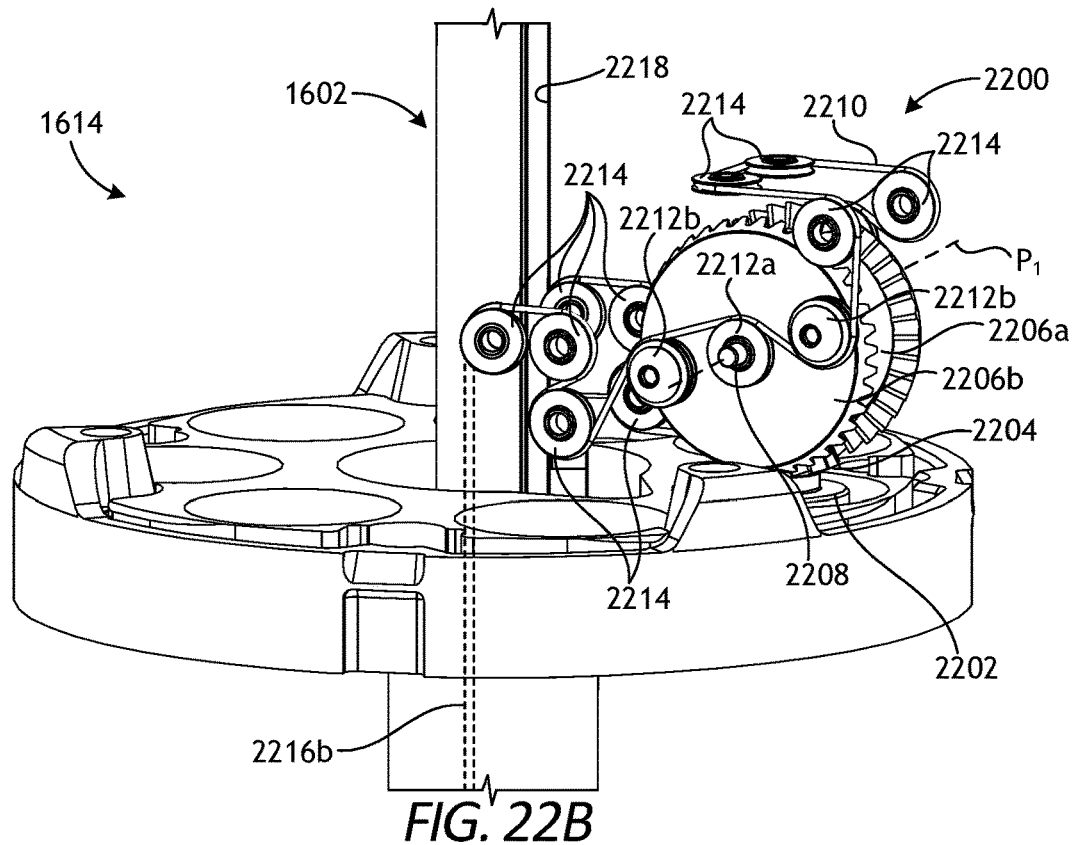

FIGS. 22A and 22B are opposing isometric side views of another example accumulator system 2200 that may be incorporated into the handle 1614, according to one or more additional embodiments. The outer body of the handle 1614 and various other accumulator systems and component parts of the handle 1614 are omitted in FIGS. 22A-22B to enable an unobstructed view of the accumulator system 2200. Similar to the accumulator system 1800 of FIG. 18, the accumulator system 2200 may be operable (actuatable) to carry out a variety of functions (operations) of the surgical tool 1600 (FIG. 16). In some embodiments, for example, operation of the accumulator system 2200 may cause the end effector 1604 (FIG. 16) to articulate at the wrist 1606 (FIGS. 16-17). In other embodiments, however, the accumulator system 2200 may be operable to "fire" the end effector 1604, as generally described herein.

As illustrated, the accumulator system 2200 may include or may be operatively coupled to a drive input 2202 rotatably mounted to the handle 1614. The drive input 2202 may be the same as or similar to any of the drive inputs 1620a-f of FIGS. 16-17 and, therefore, may be matable with and driven by a corresponding drive output of the instrument driver 1618 (FIGS. 16-17), such as any of the drive outputs 1718a-f of FIG. 17. A beveled pinion gear 2204 (mostly occluded) may be coupled to or form an integral part of the drive input 2202 such that rotation of the drive input 2202 will correspondingly rotate the beveled pinion gear 2204 in the same angular direction.

The accumulator system 2200 may further include at least one bevel gear arranged to intermesh with the beveled pinion gear 2204 such that rotation of the beveled pinion gear 2204 correspondingly rotates the bevel gear. In the illustrated embodiment, the accumulator system 2200 includes a first bevel gear 2206a and a second bevel gear 2206b laterally offset from the first bevel gear 2206a. The bevel gears 2206a,b may each be rotatably mounted to an axle 2208 secured within the handle 1614 and the bevel gears 2206a,b may be able to rotate about a pivot axis $P_1$ extending along the axle 2208.

As illustrated, the bevel gears 2206a,b may each be arranged within the handle 1614 facing each other such that gear teeth defined on each bevel gear 2206a,b intermeshes with gear teeth defined on the beveled pinion gear 2204. In the depicted opposing arrangement of the bevel gears 2206a,b, rotation of the beveled pinion gear 2204 will correspondingly cause the bevel gears 2206a,b to rotate in opposite angular directions about the pivot axis $P_1$. In the illustrated embodiment, a gear reduction of 2.5:1 is shown between the beveled pinion gear 2204 and the bevel gears 2206a,b. Those skilled in the art, however, will readily appreciate that the gear reduction ratio may be increased or decreased to achieve higher cable speed or tension, as required by the application.

The accumulator system 2200 may further include a drive member 2210 that extends longitudinally along at least a portion of the shaft 1602. In the illustrated embodiment, the drive member 2210 comprises a cable or wire and, therefore, will be referred to herein as "the drive cable 2210". In other embodiments, however, the drive cable 2210 may comprise any of the other types of drive members mentioned herein.

As illustrated, the drive cable 2210 may extend or be threaded (guided) through the accumulator system 2200 within the body of the handle 1614. More specifically, the accumulator system 2200 may include a series of strategically arranged pulleys configured to guide and direct the drive cable 2210 to and from the shaft 1602 and through the accumulator system 2200. The accumulator system 2200 may include, for example, a plurality of accumulator pulleys rotatably mounted to each bevel gear 2206a,b. In the illustrated embodiment, a center accumulator pulley 2212a and two outer accumulator pulleys 2212b may be rotatably mounted to a planar, back surface of each bevel gear 2206a,b. The center accumulator pulley 2212a may be rotatably mounted to the axle 2208, and the outer accumulator pulleys 2212b may be rotatably mounted to the corresponding bevel gear 2206a,b at or near an outer periphery of the bevel gear 2206a,b. In some embodiments, as illustrated, the accumulator pulleys 2212a,b may be linearly aligned and in a common plane, but could alternatively be non-linearly aligned, without departing from the scope of the disclosure.

The accumulator system 2200 may further include a plurality of idler pulleys 2214 rotatably coupled to the handle 1614 and arranged to redirect the drive cable 2210 between the shaft 1602 and the accumulator pulleys 2212a,b. While depicted in FIGS. 22A-22B as floating (unsupported), the idler pulleys 2214 will be rotatably coupled to various structural elements or stationary features of the handle 1614 not shown in FIGS. 22A-22B. In the illustrated embodiment, twelve idler pulleys 2214 are included in the accumulator system 2200, but more or less than twelve may be included, without departing from the scope of the disclosure. Moreover, the orientation and location of the idler pulleys 2214 depicted in FIGS. 22A-22B is merely one example of how the idler pulleys 2214 may be arranged. Indeed, the orientation and location of the idler pulleys 2214 may vary depending on the orientation of the bevel gears 2206a,b within the handle 1614, or based on a particular application, without departing from the scope of the disclosure.

As illustrated, the idler pulleys 2214 are strategically arranged within the handle 1614 to redirect the drive cable 2210 to and from the shaft 1602 and through the accumulator system 2200. More specifically, the idler pulleys 2214 may be arranged to redirect the drive cable 2210 in sequence from the shaft 1602, to the accumulator pulleys 2212a,b of one of the bevel gears 2206a,b, to the accumulator pulleys 2212a,b mounted to the other bevel gear 2206a,b, and back to the shaft 1602. At the shaft 1602, the drive cable 2210 may be extend distally along the shaft 1602 as first and second drive cable portions 2216a and 2216b. In some embodiments, one or both of the drive cable portions 2216a,b may be received and extend within one or more grooves 2218 (one shown) defined in the shaft 1602. In other embodiments, however, the drive cable portions 2216a,b may alternatively be received within the interior of the shaft 1602 or extend along an exterior surface of the shaft 1602, without departing from the scope of the disclosure.

The drive cable portions 2216a,b may extend distally to be operatively coupled to one or both of the end effector 1604 (FIG. 16) and the wrist 1606 (FIGS. 16-17). In some embodiments, actuation or operation of the accumulator system 2200 may result in antagonistic manipulation of the drive cable portions 2216a,b along the shaft 1602, which can help facilitate one or more functions of the end effector 1604 or the wrist 1606, such as causing the end effector 1604 to articulate or fire. More specifically, rotation of the drive input 2202 will correspondingly rotate the beveled pinion gear 2204 and cause the bevel gears 2206a,b to rotate in opposite angular directions about the pivot axis $P_1$. Rotating the bevel gears 2206a,b will correspondingly rotate the accumulator pulleys 2212a,b mounted to each bevel gear 2206a,b, and thus cause the drive cable 2210 to either become more or less wrapped about (onto) the accumulator pulleys 2212a,b.

In example operation, rotating the drive input 2202 in a first direction will rotate the beveled pinion gear 2204 in the same direction and thereby cause the first bevel gear 2206a to rotate in a first angular direction (e.g., clockwise) and the second bevel gear 2206b to rotate in a second angular direction opposite the first angular direction (e.g., counter-clockwise). As the first bevel gear 2206a rotates in the first angular direction, the accumulator pulleys 2212a,b mounted to the first bevel gear 2206a will correspondingly rotate and pull or pay in (draw in) a length of the first drive cable portion 2216a. In contrast, as the second bevel gear 2206b rotates in the second angular direction, the accumulator pulleys 2212a,b mounted to the second bevel gear 2206b will correspondingly rotate and pay out (dispense) a length of the second drive cable portion 2216b to the shaft 1602.

Figure 23A:
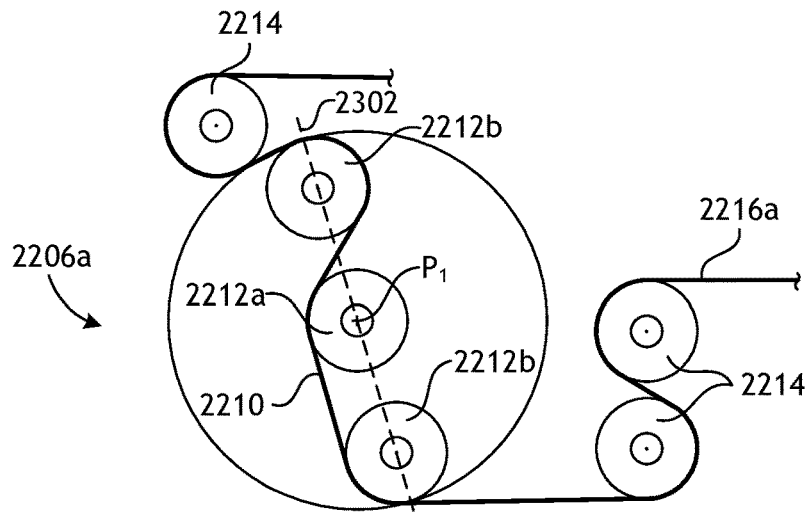
FIGS. 23A-23C are progressive, schematic side views of the first bevel gear during example operation of the accumulator system of FIGS. 22A-22B, according to one or more embodiments.
Figure 23B:
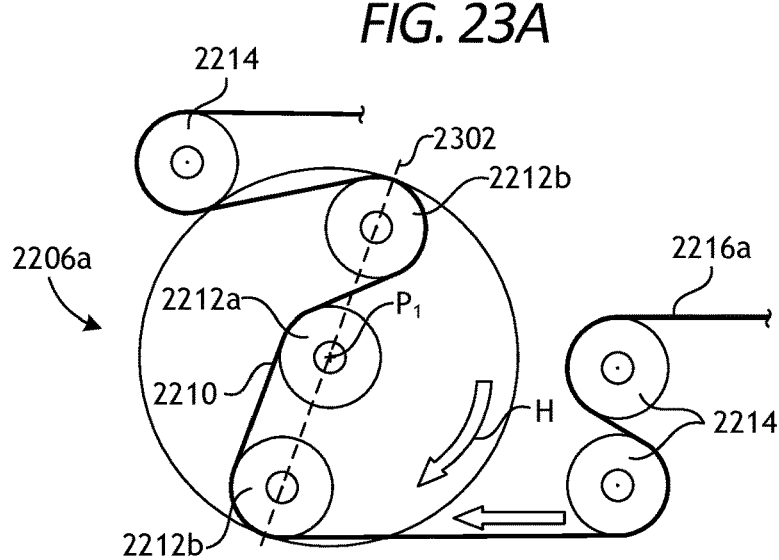
Figure 23C:
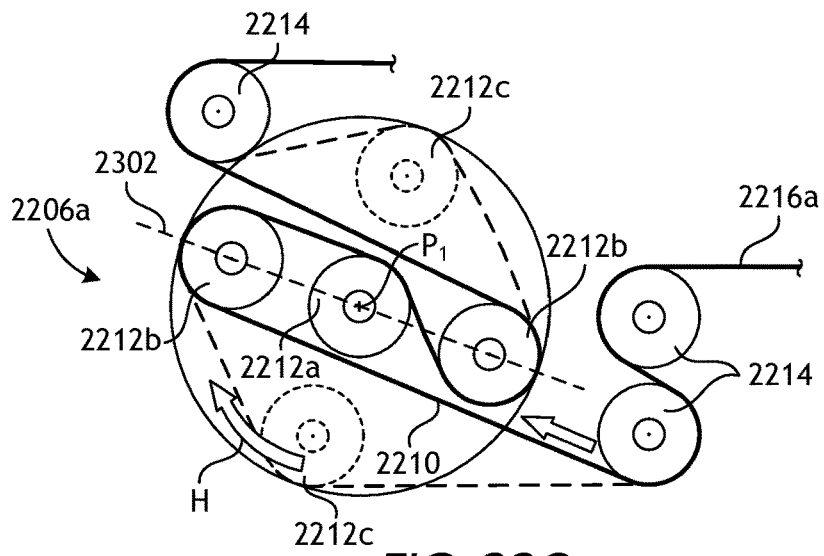

FIGS. 23A-23C are progressive, schematic side views of the first bevel gear 2206a during example operation of the accumulator system 2200 of FIGS. 22A-22B, according to one or more embodiments. While directed to operation of the first bevel gear 2206a, the following discussion is equally applicable to the second bevel gear 2206b. As illustrated, the accumulation pulleys 2212a,b may be mounted to the first bevel gear 2206a and rotatable about the pivot axis $P_1$ as the first bevel gear 2206a rotates. Moreover, as mentioned above, the accumulation pulleys 2212a,b may be arranged linearly and otherwise along a common line 2302, but could alternatively be mounted non-linearly. The idler gears 2214 may be arranged to feed and guide the drive cable 2210 (e.g., the first drive cable portion 2216a) to and from the accumulator pulleys 2212a,b.

Referring first to FIG. 23A, as mentioned above, rotation of the beveled pinion gear 2204 (FIGS. 22A-22B) causes the first bevel gear 2206a to rotate about the pivot axis $P_1$ and simultaneously rotate the accumulator pulleys 2212a,b in the same direction. In FIG. 23B, the first bevel gear 2206a is rotated in a first angular direction H (e.g., clockwise), which rotates the accumulator pulleys 2212a,b in the same direction and thereby pulls or pays in (draws in) a length of the first drive cable portion 2216a from the shaft 1602 (FIGS. 22A-22B) as the drive cable 2210 becomes more wrapped about the accumulator pulleys 2212a,b. Rotating the first bevel gear 2206a even further in the first angular direction H, as shown in FIG. 23C, will rotate the accumulator pulleys 2212a,b even further in the same direction and thereby progressively pull or pay in (draw in) additional length of the first drive cable portion 2216a from the shaft 1602 as the drive cable 2210 becomes even more wrapped about the accumulator pulleys 2212a,b.

In some embodiments, as shown in FIG. 23C, one or more additional outer accumulator pulleys 2212c (two shown) may be rotatably mounted to the first bevel gear 2206a. The additional outer accumulator pulleys 2212c may be included to help increase the amount of the first drive cable portion 2216a that may be paid in (drawn in) as the first bevel gear 2206a rotates in the first angular direction H, thus resulting in a longer stroke of the drive cable 2210 along the shaft 1602 (FIGS. 22A-22B).

Referring again the FIGS. 22A-22B, the drive cable portions 2216a,b may extend distally along the shaft 1602 from the accumulator system 2200 and may be operatively coupled to one or both of the end effector 1604 (FIG. 16) and the wrist 1606 (FIGS. 16-17). Consequently, operation of the accumulator system 2200 may result in antagonistic manipulation of the drive cable portions 2216a,b along the shaft 1602 to help operate the end effector 1604 or the wrist 1606. For example, and with additional reference to FIG. 19, in some embodiments, the drive cable portions 2216a,b may extend to the wrist 1616 and may be operatively coupled to the distal link 1904 (FIG. 19). As the first drive cable portion 2216a is drawn into the accumulator pulleys 2212a,b of the first bevel gear 2206a, the second drive cable portion 2216b is simultaneously paid out (dispensed) to the shaft 1602 from the accumulator pulleys 2212a,b of the second bevel gear 2206b. Reversing operation of the accumulator system 2200 results in the second drive cable portion 2216b being drawn into the accumulator pulleys 2212a,b of the second bevel gear 2206b, the first drive cable portion 2216a being simultaneously paid out (dispensed) to the shaft 1602 from the accumulator pulleys 2212a,b of the first bevel gear 2206a. This equal and opposite movement of the drive cable portions 2216a,b cooperatively acts on the end effector mount 1902 (FIG. 19) via the distal link 1904 to cause the end effector 1604 (FIG. 19) to rotate either clockwise $G_1$ or counter-clockwise $G_2$.

In other embodiments, and with additional reference to FIGS. 21A-21B, the drive cable portions 2216a,b may alternatively extend to the knife drive system 2100 of FIGS. 21A-21B, where the first drive cable portion 2216a may be coupled to and terminate at the collar 2104 (FIGS. 21A-21B), and the second drive cable portion 2216b may loop around the pulley 2106 (FIG. 21A) and may also be coupled to the collar 2104. Operating the accumulator system 2200 as described above may selectively load the drive cable portions 2216a,b in tension and thereby cause the drive rod 2006 (FIGS. 21A-21B) and the knife 2002 (FIGS. 21A-21B) to move distally or proximally as coupled to the collar 2104.

In some embodiments, the accumulator system 2200 may be decoupled from shaft 1602 insertion. More specifically, the accumulator pulleys 2212a,b and the idler pulleys 2214 are able to freely rotate (e.g., "free wheel") and are otherwise not driven during operation of the handle 1614. Consequently, as the shaft 1602 moves longitudinally relative to the handle 1614 in z-axis translation, the drive cable 2210 is able to freely run (course) through the accumulator system 2200 and through the accumulator and idler pulleys 2212a,b, 2214. Moreover, since the accumulator and idler pulleys 2212a,b, 2214 are able to freely rotate, the accumulator system 2200 can be operated simultaneously during shaft 1602 translation.

In some embodiments, one of the outer accumulator pulleys 2212b (or one of the idler pulleys 2214) may alternatively (or in addition thereto) comprise a spring-loaded tensioning pulley. In such embodiments, the spring-loaded tensioning pulley may continuously act on the drive cable 2210 to remove slack and otherwise mitigate cable stretch in the drive cable 2210. Moreover, in such embodiments, the spring-loaded tensioning pulley may exhibit sufficient spring force to reverse direction of the drive cable pulleys 2216a,b after operation of the accumulator system 2200 ceases. Consequently, the spring-loaded tensioning pulley may be capable of reversing actuation or firing at the end effector (FIGS. 19-20), such as being capable of retracting the knife 2002 (FIGS. 21A-21B) autonomously.

Figure 24:
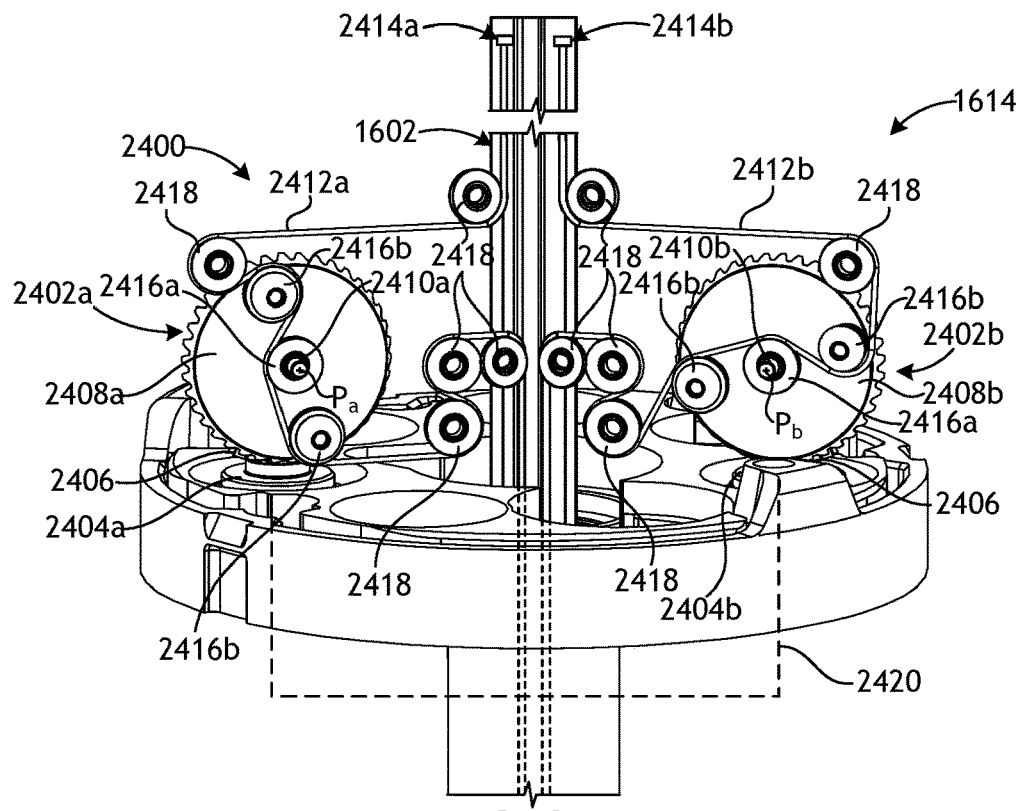
FIG. 24 is an isometric side view of another example accumulator system that may be incorporated into the handle of FIGS. 16-17, according to one or more additional embodiments.

FIG. 24 is an isometric side view of another example accumulator system 2400 that may be incorporated into the handle 1614, according to one or more additional embodiments. As with FIGS. 22A-22B, the outer body of the handle 1614 and various other accumulator systems and component parts of the handle 1614 are omitted in FIG. 24 to enable an unobstructed view of the accumulator system 2400. Similar to the accumulator systems 1800 and 2200 of FIGS. 18 and 22A-22B, respectively, the accumulator system 2400 may be operable (actuatable) to carry out a variety of functions (operations) of the surgical tool 1600 (FIG. 16). In some embodiments, for example, operation of the accumulator system 2400 may cause the end effector 1604 (FIG. 16) to articulate at the wrist 1606 (FIGS. 16-17). In other embodiments, however, the accumulator system 2400 may be operable to fire the end effector 1604, as generally described herein.

As illustrated, the accumulator system 2400 may include first and second bevel gear assemblies 2402a and 2402b. The first bevel gear assembly 2402a may be operatively coupled to a first drive input 2404a rotatably mounted to the handle 1614, and the second bevel gear assembly 2402b may be operatively coupled to a second drive input 2404b rotatably mounted to the handle 1614. The drive inputs 2404a.b may be the same as or similar to any of the drive inputs 1620a-f of FIGS. 16-17 and, therefore, may be matable with and driven by corresponding drive outputs of the instrument driver 1618 (FIGS. 16-17), such as any of the drive outputs 1718a-f of FIG. 17. Each bevel gear assembly 2402a,b may further include a beveled pinion gear 2406 (mostly occluded) coupled to or forming an integral part of the corresponding drive input 2404a,b such that rotation of the drive input 2404a,b will rotate the corresponding beveled pinion gear 2406 in the same angular direction.

Each bevel gear assembly 2402a,b may further include at least one bevel gear arranged to intermesh with the corresponding beveled pinion gear 2406. In the illustrated embodiment, the first bevel gear assembly 2402a includes a first bevel gear 2408a and the second bevel gear assembly 2402b includes a second bevel gear 2408b. Each bevel gear 2408a may be rotatably mounted to a corresponding axle 2410a and 2410b secured within the handle 1614, and the bevel gears 2408a,b may be able to rotate about corresponding pivot axes $P_a$ and $P_b$ extending along the axles 2410a,b.

As illustrated, the bevel gears 2408a,b may each be arranged within the handle 1614 such that gear teeth defined on each bevel gear 2408a,b intermeshes with gear teeth defined on the corresponding beveled pinion gear 2406. Consequently, rotation of the beveled pinion gear 2406 will correspondingly rotate the intermeshed bevel gear 2408a,b about the corresponding pivot axes $P_{a,b}$.

The first bevel gear assembly 2402a may further include a first drive member 2412a that extends longitudinally along at least a portion of the shaft 1602, and the second bevel gear assembly 2402b may further include a second drive member 2412b that extends longitudinally along at least a portion of the shaft 1602. The drive members 2412a,b comprise a cable or wire and, therefore, will be referred to herein as "drive cables 2412a,b". In other embodiments, however, the drive cables 2412a,b may comprise any of the other types of drive members mentioned herein.

In some embodiments, a first end 2414a of the first drive cable 2412a may be anchored to the shaft 1602 above (proximal to) the handle 1614, and a first end 2414b of the second drive cable 2412b may be similarly anchored to the shaft 1602 above (proximal to) the handle 1614. As will be appreciated, the first ends 2414a,b of the drive cables 2412a,b may be anchored to the shaft 1602 at a sufficient distance to allow the shaft 1602 to be able to travel through handle 1614 in z-axis translation. Moreover, the second ends of each drive cable 2412a,b may extend distally along the shaft 1602 to the end effector 1604 (FIG. 16) and/or the wrist 1606 (FIGS. 16-17) and may thereby help facilitate one or more functions of the end effector 1604 or the wrist 1606, such as causing the end effector 1604 to articulate or fire.

As illustrated, the drive cables 2412a,b may extend or be threaded (guided) through the accumulator system 2400 within the body of the handle 1614. More specifically, each bevel gear assembly 2402a,b may include a series of strategically arranged pulleys configured to guide and direct the drive cables 2412a,b to and from the shaft 1602 and through the accumulator system 2400. Each bevel gear assembly 2402a,b may include, for example, a plurality of accumulator pulleys rotatably mounted to each bevel gear 2408a,b. In the illustrated embodiment, each bevel gear assembly 2402a,b includes a center accumulator pulley 2416a and two outer accumulator pulleys 2416b rotatably mounted to a planar, back surface of each bevel gear 2408a,b. The center accumulator pulley 2416a may be rotatably mounted to the corresponding axle 2410a,b, and the outer accumulator pulleys 2416b may be rotatably mounted to the corresponding bevel gear 2408a,b at or near an outer periphery of the bevel gear 2408a,b. In some embodiments, as illustrated, the accumulator pulleys 2416a,b may be linearly aligned and in a common plane, but could alternatively be non-linearly aligned, without departing from the scope of the disclosure. The center accumulator pulley 2416a may help facilitate directional cable management by allowing the outer accumulator pulleys 2416b to affect cable accumulation during operation.

Each bevel gear assembly 2402a,b may further include a plurality of idler pulleys 2418 rotatably coupled to the handle 1614 and arranged to redirect the drive cables 2412a,b between the shaft 1602 and the corresponding accumulator pulleys 2416a,b. While depicted in FIG. 24 as floating (unsupported), the idler pulleys 2418 will be rotatably coupled to various structural elements or stationary features of the handle 1614 not shown in FIG. 24. In the illustrated embodiment, each bevel gear assembly 2402a,b includes five idler pulleys 2418, but more or less than five may be included, without departing from the scope of the disclosure. As illustrated, the idler pulleys 2418 are strategically arranged within the handle 1614 to redirect the drive cables 2412a,b to and from the shaft 1602 and through the corresponding bevel gear assemblies 2402a,b. Moreover, the orientation and location of the idler pulleys 2418 depicted in FIG. 24 is merely one example of how the idler pulleys 2418 may be arranged. Indeed, the orientation and location of the idler pulleys 2418 may vary depending on the orientation of the bevel gears 2408a,b within the handle 1614, or based on the particular application, without departing from the scope of the disclosure.

Rotation of the drive inputs 2404a,b will correspondingly rotate the beveled pinion gears 2406, which causes the corresponding bevel gears 2408a,b to rotate about the respective pivot axes $P_{a,b}$. Rotating the bevel gears 2408a,b will correspondingly rotate the corresponding accumulator pulleys 2416a,b mounted to each bevel gear 2408a,b, and thus cause the drive cable 2412a to either become more or less wrapped about (onto) the accumulator pulleys 2416a,b.

In example operation, rotating the first drive input 2404a in a first direction will rotate the corresponding beveled pinion gear 2406 in the same direction and thereby cause the first bevel gear 2408a to rotate in a first angular direction (e.g., clockwise). As the first bevel gear 2408a rotates in the first angular direction, the accumulator pulleys 2416a,b mounted to the first bevel gear 2408a will correspondingly rotate and pull or pay in (draw in) a length of the first drive cable 2412a from the shaft 1602. In contrast, rotating the second drive input 2404b in a second direction will rotate the corresponding beveled pinion gear 2406 in the same direction and thereby cause the second bevel gear 2408b to rotate in a second angular direction (e.g., counter-clockwise). As the second bevel gear 2408b rotates in the second angular direction, the accumulator pulleys 2416a,b mounted to the second bevel gear 2408a will correspondingly rotate and pay out (dispense) a length of the second drive cable portion 2216b to the shaft 1602. Reversing operation of the drive inputs 2404a,b will result in the accumulator pulleys 2416a,b mounted to the first bevel gear 2408a paying out (dispensing) a length of the first drive cable 2412a to the shaft 1602, and the accumulator pulleys 2416a,b mounted to the second bevel gear 2408a rotating and paying in (drawing in) a length of the second drive cable 2412b from the shaft 1602.

As indicated above, the drive cables 2412a,b may extend distally to be operatively coupled to one or both of the end effector 1604 (FIG. 16) and the wrist 1606 (FIGS. 16-17). Accordingly, operation of the accumulator system 2400 may result in antagonistic movement (manipulation) of the drive cables 2412a,b along the shaft 1602, which can help facilitate one or more functions of the end effector 1604 or the wrist 1606. For example, in some embodiments, the drive cables 2412a,b may extend to the wrist 1616 and may be operatively coupled to the distal link 1904 (FIG. 19). In such embodiments, actuation of the first bevel gear assembly 2402a in a first direction may pay in a portion of the first drive cable 2412a while actuation of the second gear assembly 2402b in the first direction may simultaneously pay out a portion of the second drive cable 2412b. In contrast, actuation of the first bevel gear assembly 2402a in a second direction may pay out a portion of the first drive cable 2412a while actuation of the second gear assembly 2402b in the section direction may simultaneously pay in a portion of the second drive cable 2412b. Such antagonistic manipulation of the drive cables 2412a,b may cooperatively act on the end effector mount 1902 (FIG. 19) via the distal link 1904 to cause the end effector 1604 (FIG. 19) to rotate either clockwise $G_1$ or counter-clockwise $G_2$.

In other embodiments, the drive cables 2412a,b may extend to the knife drive system 2100 of FIGS. 21A-21B, where the first drive cable 2412a may be coupled to and terminate at the collar 2104 (FIGS. 21A-21B), and the second drive cable 2412b may loop around the pulley 2106 (FIG. 21A) and may also be coupled to the collar 2104. Selective antagonistic actuation of the drive cables 2412a,b, via operation of the accumulator system 2400, may cause the drive rod 2006 (FIGS. 21A-21B) and the knife 2002 (FIGS. 21A-21B) to move distally or proximally as coupled to the collar 2104.

The foregoing embodiment may be advantageous in eliminating the need of an internal tensioning mechanism for the drive cables 2412a,b. Instead, antagonistic operation of the bevel gear assemblies 2402a,b may facilitate an antagonistic control scheme to tension the drive cables 2412a,b and remove the need for a tensioning mechanism. In some embodiments, the accumulator system 2400 may be decoupled from shaft 1602 insertion. More specifically, the accumulator pulleys 2416a,b and the idler pulleys 2418 are able to freely rotate (e.g., "free wheel") and are otherwise not driven during operation of the handle 1614. Consequently, as the shaft 1602 moves longitudinally relative to the handle 1614 in z-axis translation, the drive cable 2210 is able to freely run (course) through the accumulator system 2200 and through the accumulator and idler pulleys 2416a,b, 2418. Moreover, since the accumulator and idler pulleys 2416a,b, 2418 are able to freely rotate, the accumulator system 2400 can be operated simultaneously during shaft 1602 translation.

In one or more embodiments, operation of the beveled pinion gears 2406 may be mechanically linked such that rotation of the first drive input 2404a (or alternatively the second drive input 2404b) rotates each pinion gear 2406 simultaneously. As will be appreciated, this may prove advantageous in synchronizing pay-in and pay-out of the drive cables 2412a,b while only requiring a single drive input. In such embodiments, a mechanical linkage 2420 (shown as a dashed line) may extend between and mechanically interconnect the individual beveled pinion gears 2406. The mechanical linkage 2420 may comprise any known means of mechanically linking rotating gears, an interconnected gear train or one or more wires or cables extending between the two pinion gears 2406.

Figure 25:
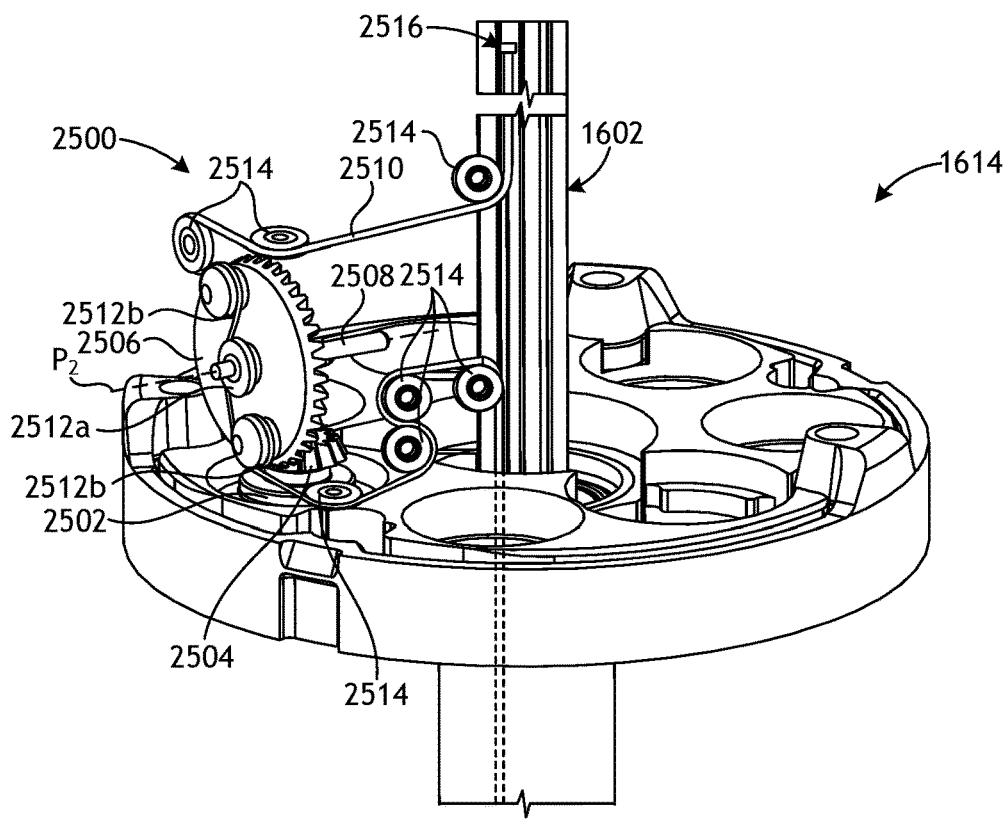
FIG. 25 is an isometric side view of another example accumulator system that may be incorporated into the handle of FIGS. 16-17, according to one or more additional embodiments.

FIG. 25 is an isometric side view of another example accumulator system 2500 that may be incorporated into the handle 1614, according to one or more additional embodiments. As with FIGS. 22A-22B and 24, the outer body of the handle 1614 and various other accumulator systems and component parts of the handle 1614 are omitted in FIG. 25 to enable an unobstructed view of the accumulator system 2500.

As illustrated, the accumulator system 2500 may include or may be operatively coupled to a drive input 2502 rotatably mounted to the handle 1614. The drive input 2502 may be the same as or similar to any of the drive inputs 1620a-f of FIGS. 16-17 and, therefore, may be matable with and driven by a corresponding drive output of the instrument driver 1618 (FIGS. 16-17), such as any of the drive outputs 1718a-f (FIG. 17). A beveled pinion gear 2504 may be coupled to or form an integral part of the drive input 2502 such that rotation of the drive input 2502 will correspondingly rotate the beveled pinion gear 2504 in the same angular direction.

The accumulator system 2500 may further include a bevel gear 2506 arranged to intermesh with the beveled pinion gear 2504. While one bevel gear 2506 is depicted in FIG. 25, and two bevel gears 2206a,b and 2408a,b are depicted FIGS. 22A-22B and 24, respectively, those skilled in the art will appreciate that more than two bevel gears may be used, without departing from this disclosure. The bevel gear 2506 may be rotatably mounted to an axle 2508 secured within the handle 1614 and the bevel gear 2506 may be able to rotate about a pivot axis $P_2$ extending along the axle 2508. The orientation of the bevel gear 2506 within the handle 1614 may adjusted in any direction such that the bevel gear 2506 is positioned in any orientation to fit the particular application or packaging within the handle 1614. Moreover, in the illustrated embodiment, a gear reduction of 2.5:1 is shown between the beveled pinion gear 2504 and the bevel gear 2506. Those skilled in the art, however, will readily appreciate that the gear reduction ratio and/or the size of the beveled pinion gear 2504 and the bevel gear 2506 may be increased or decreased to achieve higher cable speed or tension, as required by the application. For example, changing the diameter of one or both of the gears 2504, 2506 can affect various load configurations with a tradeoff of sizing. This may also prove advantageous in enabling increased cable accumulation or increased end effector function travel distance.

The accumulator system 2500 may further include a drive member 2510 that extends longitudinally along at least a portion of the shaft 1602. In the illustrated embodiment, the drive member 2510 comprises a cable or wire and, therefore, will be referred to herein as "the drive cable 2510". In other embodiments, however, the drive cable 2510 may comprise any of the other types of drive members mentioned herein.

The accumulator system 2500 may include a series of strategically arranged pulleys configured to guide and direct the drive cable 2510 to and from the shaft 1602 and through the accumulator system 2500. The accumulator system 2500 may include, for example, a center accumulator pulley 2512a and two outer accumulator pulleys 2512b rotatably mounted to a planar, back surface of the bevel gear 2506. The center accumulator pulley 2512a may be rotatably mounted to the axle 2508, and the outer accumulator pulleys 2512b may be rotatably mounted at or near an outer periphery of the bevel gear 2506. In some embodiments, as illustrated, the accumulator pulleys 2512a,b may be linearly aligned and arranged in a common plane, but could alternatively be non-linearly aligned, without departing from the scope of the disclosure. The center accumulator pulley 2512a may help facilitate directional cable management by allowing the outer accumulator pulleys 2512b to affect cable accumulation during operation.

The accumulator system 2500 may further include a plurality of idler pulleys 2514 rotatably coupled to the handle 1614 and arranged to redirect the drive cable 2510 between the shaft 1602 and the accumulator pulleys 2512a,b. While depicted in FIG. 25 as floating (unsupported), the idler pulleys 2514 will be rotatably coupled to various structural elements or stationary features of the handle 1614 not shown in FIG. 25. In the illustrated embodiment, seven idler pulleys 2514 are included in the accumulator system 2500, but more or less than seven may be included, without departing from the scope of the disclosure. Moreover, the orientation and location of the idler pulleys 2514 depicted in FIG. 25 is merely one example of how the idler pulleys 2514 may be arranged. Indeed, the orientation and location of the idler pulleys 2514 may vary depending on the orientation of the bevel gear 2506 within the handle 1614, or based on the particular application, without departing from the scope of the disclosure.

As illustrated, the idler pulleys 2514 are strategically arranged within the handle 1614 to redirect the drive cable 2510 to and from the shaft 1602 and through the accumulator system 2500. More specifically, the idler pulleys 2514 may be arranged to redirect the drive cable 2510 in sequence from the shaft 1602, to the accumulator pulleys 2512a,b, and back to the shaft 1602. In some embodiments, a first end 2516 of the drive cable 2510 may be anchored to the shaft 1602 above (proximal to) the handle 1614, and the second end (not shown) may extend distally along the shaft 1602 to the end effector 1604 (FIG. 16) and/or the wrist 1606 (FIGS. 16-17) to help facilitate one or more functions of the end effector 1604 or the wrist 1606. As will be appreciated, the first end 2516 of the drive cable 2510 may be anchored to the shaft 1602 at a sufficient distance to allow the shaft 1602 to be able to travel through handle 1614 in z-axis translation. In other embodiments, however, the first end 2516 may also extend distally to the end effector 1604 and/or the wrist 1606, and the drive cable 2510 may operate as an antagonistic closed-loop system, without departing from the scope of the disclosure.

Operation of the accumulator system 2500 is substantially similar to operation of the accumulator systems 2200 and 2400 of FIGS. 22A-22B and 24, respectively. Briefly, rotation of the drive input 2502 will correspondingly rotate the beveled pinion gear 2504, which causes the bevel gear 2506 to rotate about the pivot axis $P_2$, which correspondingly rotates the accumulator pulleys 2512a,b and causes the drive cable 2510 to either become more or less wrapped about (onto) the accumulator pulleys 2512a,b. As the accumulator pulleys 2512a,b rotate and interact with the drive cable 2510, and depending on the rotation direction, the accumulator system 2500 will pay in (draw in) a length of the drive cable 2510 from the shaft 1602 or pay out (dispense) a length of the drive cable 2510 to the shaft 1602.

In some embodiments, the accumulator system 2500 may be decoupled from shaft 1602 insertion. More specifically, the accumulator pulleys 2512a,b and the idler pulleys 2514 are able to freely rotate (e.g., "free wheel") and are otherwise not driven during operation of the handle 1614. Consequently, as the shaft 1602 moves longitudinally relative to the handle 1614 in z-axis translation, the drive cable 2210 is able to freely run (course) through the accumulator system 2200 and through the accumulator and idler pulleys 2512a,b, 2514. Moreover, since the accumulator and idler pulleys 2512a,b, 2514 are able to freely rotate, the accumulator system 2500 can be operated simultaneously during shaft 1602 translation.

Counter Rotation Drive Logic for Tool Shaft as Insertion Lead Screw

Figure 26A:
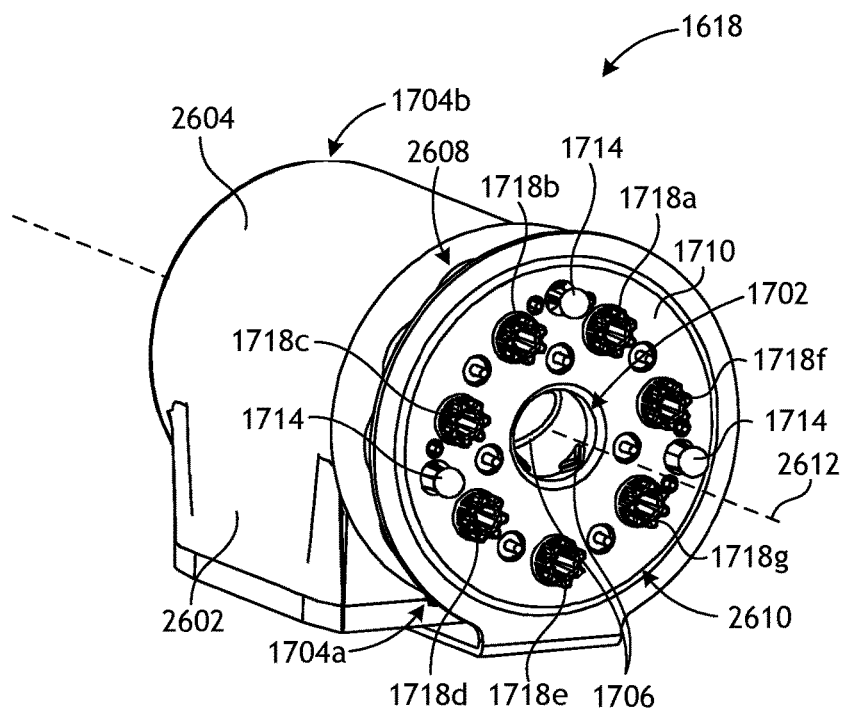
FIG. 26A is a perspective view of the instrument driver of FIG. 17.
Figure 26B:
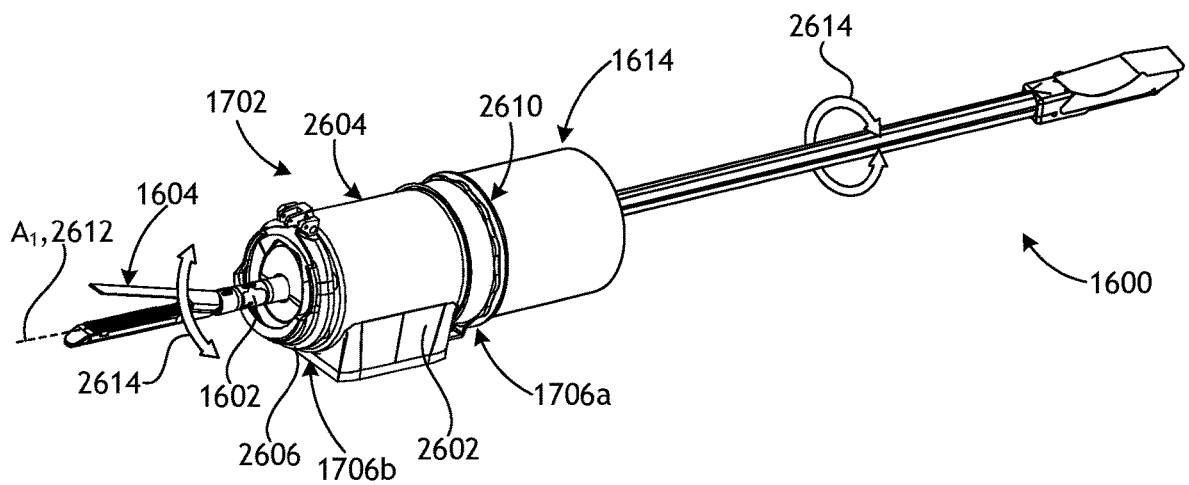
FIG. 26B is an isometric view of the surgical tool of FIG. 16 releasably coupled to the instrument driver of FIG. 26A.

FIG. 26A is a perspective view of the instrument driver 1618 of FIG. 17, and FIG. 26B is an isometric view of the surgical tool 1600 of FIG. 16 releasably coupled to the instrument driver 1618, according to one or more embodiments. As briefly discussed above, the instrument driver 1618 is configured to attach a surgical tool (e.g., the surgical tool 1600) to a surgical robotic arm (e.g., any of the robotic arms 104, 406 described herein). More specifically, the drive interface 1710 at the first end 1704a of the instrument driver 1618 is matable with the driven interface 1712 (FIG. 17) of the handle 1614. The end effector 1604 and the shaft 1602 can penetrate the instrument driver 1618 by extending through the central aperture 1702 defined longitudinally through the instrument driver 1618, and the alignment guides 1706 within the central aperture 1702 help angularly orient the surgical tool 1600 to the proper orientation relative to the instrument driver 1618.

In some embodiments, the handle 1614 may be mechanically coupled to the instrument driver 1618 by mating the interlocking features 1714 provided at the drive interface 1710 with the complementary-shaped pockets 1716 (FIG. 17) provided on the driven interface 1712 (FIG. 17) of the handle 1614. Moreover, the instrument driver 1618 includes the drive outputs 1718a-f that are matable with the drive inputs 1620a-f (FIG. 17) of the handle 1614 such that, once properly mated, the drive inputs 1620a-f will share axes of rotation with the corresponding drive outputs 1718a-f to allow the transfer of rotational torque from the drive outputs 1718a-f to the corresponding drive inputs 1620a-f.

In the illustrated embodiment, the instrument driver 1618 includes a base 2602 that provides a location to removably mount the instrument driver 1618 to a surgical robotic arm of a surgical robotic system. Mechanical and electrical connections are provided from the robotic arm to the base 2602 and then to various mechanical and electrical components arranged within the instrument driver 1618 to manipulate and/or deliver power and/or signals from the robotic arm to the surgical tool 1600.

The instrument driver 1618 provides an outer housing 2604 that can be fixedly attached to the base 2602 and extends generally between the first and second ends 1704a,b of the instrument driver 1618. In some embodiments, the instrument driver 1618 may further include a sterile adapter 2606, 2608 that may be used to create a sterile boundary between the instrument driver 1618 and the surgical tool 1600. The sterile adapter 2606, 2608 may be configured to attach a surgical drape (not shown) to the instrument driver 1618 when the surgical tool 1600 is secured to the instrument driver 1618, and the surgical drape operates to separate the surgical tool 1600 and the patient from the instrument driver 1618 and the surgical robotics system.

The drive interface 1710, the interlocking features 1714, and the drive outputs 1718a-f are all contained within or otherwise mounted to a tool drive assembly 2610 provided at the first end 1704a of the instrument driver 1618 and extending partially into the outer housing 2604. As described herein, the tool drive assembly 2610 is capable of rotating independent of the outer housing 2604 about a rotational axis 2612. When the surgical tool 1600 is mounted to the instrument driver 1618 at the tool drive assembly 2610, the longitudinal axis $A_1$ of the surgical tool 1600 coaxially aligns with the rotational axis 2612 of the tool drive assembly 2610.

The tool drive assembly 2610 may be actuated to rotate and thereby correspondingly rotate or "roll" the entire surgical tool 1600 about its longitudinal axis $A_1$, as indicated by the arrows 2614 (FIG. 26B). Consequently, actuation of the tool drive assembly 2610 allows the entire surgical tool 1600, including the shaft 1602, the end effector 1604, and the handle 1614, to continuously roll about the longitudinal axis $A_1$ in either angular direction (i.e., clockwise or counterclockwise) relative to the base 2602 and the outer housing 2604, which remain stationary. In contrast to other surgical tools where the shaft and the end effector are rotated independent of and relative to the remaining portions of the surgical tool, the shaft 1602, the end effector 1604, and the handle 1614 are fixed in rotation, which enables the entire surgical tool 1600 to rotate as a single, monolithic unit.

Figure 27:
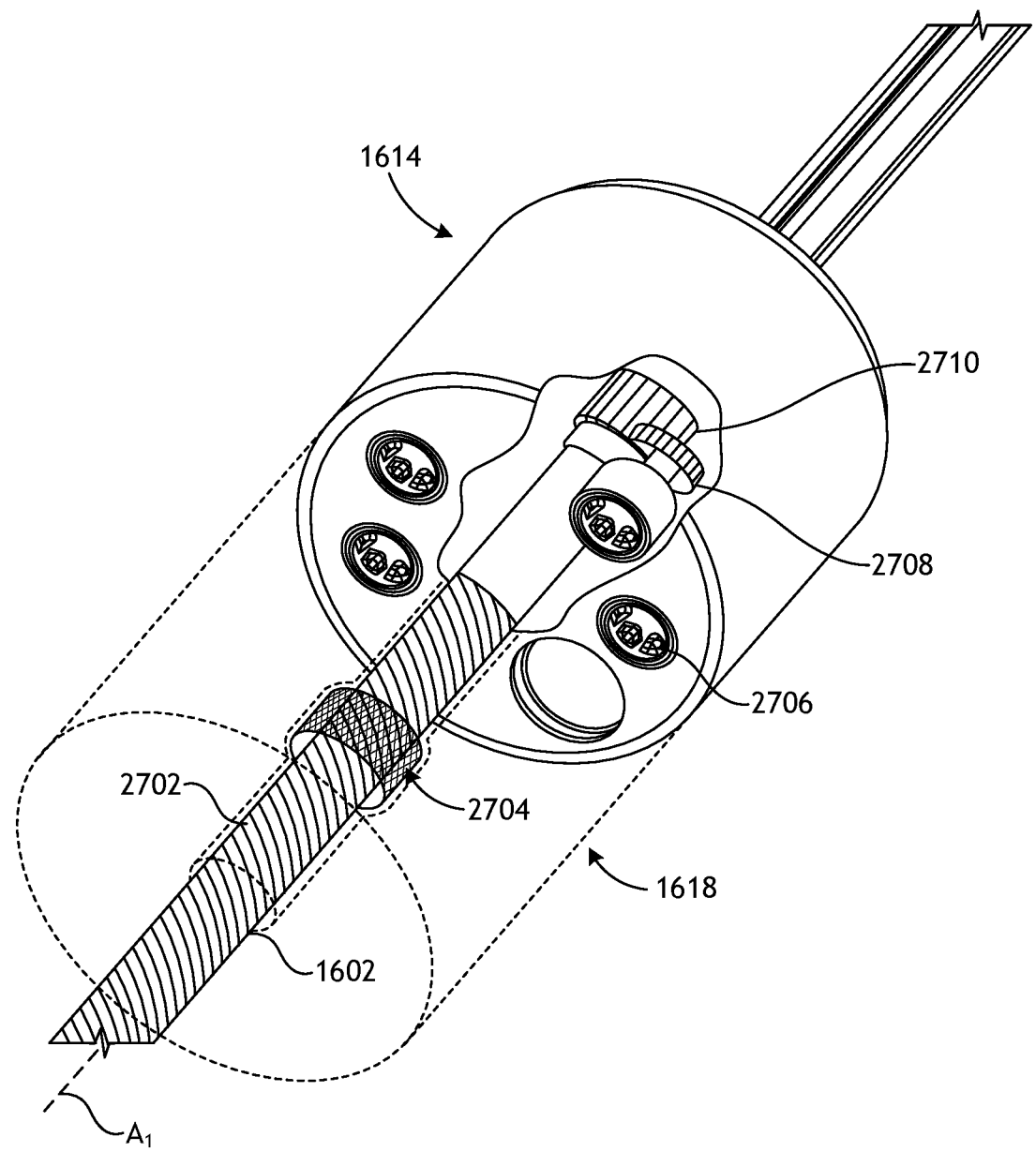
FIG. 27 is an enlarged isometric end view of an example embodiment of the handle of FIGS. 16, 17, and 26B.

FIG. 27 is an enlarged isometric end view of an example embodiment of the handle 1614 of FIGS. 16, 17, and 26B. The instrument driver 1618 is depicted in FIG. 27 in dashed lines and coupled to the handle 1614. As discussed herein, the shaft 1602 may be able to translate along the longitudinal axis $A_1$ relative to the handle 1614 and thereby achieve z-axis translation. In some embodiments, z-axis translation of the shaft 1602 may be achieved by providing external threading 2702 on the shaft 1602 and rotating a threaded nut 2704 fixed to the instrument driver 1618 as the instrument driver 1618 rotates. In such embodiments, the shaft 1602 may be coupled in a keyed or anti-rotation fashion to the handle 1614 such that the shaft 1602 is able to translate through the handle 1614 as driven by rotation of the threaded nut 2704.

In other embodiments, the handle 1614 may provide a drive input 2706, and a pinion gear 2708 may be coupled to or otherwise extend from the drive input 2706 such that rotation of the drive input 2706 correspondingly rotates the pinion gear 2708. The pinion gear 2708 may be arranged within the handle 1614 to intermesh with a driven gear 2710 fixed to the shaft 1602. As the pinion gear 2708 rotates, as driven by the drive input 2706, the driven gear 2710 will correspondingly drive the shaft 1602 in rotation. As the shaft 1602 rotates, the threaded engagement between the threaded nut 2704 and the external threading 2702 provided on the shaft 1602 may cause the shaft 1602 to translate along the longitudinal axis $A_1$ and relative to the handle 1614.

In some applications, however, it may not be desired to have the shaft 1602 rotate during z-axis translation. As described above, the tool drive assembly 2610 (FIGS. 26A-26B) of the instrument driver 1618 may be actuatable to rotate and thereby roll the entire surgical tool 1600 (i.e., clockwise or counter-clockwise) about the longitudinal axis $A_1$, including the handle 1614 and the shaft 1602. This rotation capability of the instrument driver 1618 may be used to counter the rotation of the shaft 1602 for z-axis translation, and thereby help to maintain the end effector 1604 (FIGS. 16-17) stable (i.e., non-rotating) during shaft 1602 insertion. In such embodiments, rotating the shaft 1602 in a first angular direction (e.g., clockwise) will result in z-axis translation of the shaft 1602, but the instrument driver 1618 may be simultaneously actuated to roll the entire surgical tool 1600 in a second, opposite angular direction (e.g., counter-clockwise) and at the same speed as rotation in the first angular direction. This equal but opposite rotational motion may offset the rotational motion of the shaft 1602, thus resulting in the end effector 1604 remaining rotationally stationary during z-axis translation.

3. Implementing Systems and Terminology

Implementations disclosed herein provide systems, methods and apparatus for instruments for use with robotic systems. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification which do not significantly affect the purpose of the element or number modified by such term.

To aid the Patent Office and any readers of this application and any resulting patent in interpreting the claims appended herein, applicants do not intend any of the appended claims or claim elements to invoke 35 U. S. C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical tool, comprising:
a handle providing a drive input;
an elongate shaft extendable through the handle and having an end effector arranged at a distal end of the shaft;
an accumulator system housed within the handle and operatively coupled to the drive input such that actuation of the drive input operates the accumulator system, the accumulator system including:
a beveled pinion gear coupled to the drive input;
a bevel gear arranged to intermesh with the beveled pinion gear and rotatable about an axle;
a center accumulator pulley rotatably mounted to the bevel gear at the axle;
one or more outer accumulator pulleys rotatably mounted to the bevel gear near an outer periphery of the bevel gear; and
at least one drive cable threaded through the accumulator system and extending distally along the shaft,
wherein operation of the accumulator system alters at least one of a length or a force in the at least one drive cable to affect operation of the end effector.

2. The robotic surgical tool of claim 1, further comprising:
an instrument driver arranged at an end of a robotic arm and matable with the handle,
wherein the instrument driver provides a drive output matable with the drive input, and
wherein the shaft extends through the instrument driver via a central aperture defined longitudinally through the instrument driver.

3. The robotic surgical tool of claim 1, further comprising an articulable wrist interposing the end effector and the distal end of the shaft, wherein the at least one drive cable is operatively coupled to the wrist and operation of the accumulator system acts on the at least one drive cable to articulate the end effector via the wrist.

4. The robotic surgical tool of claim 1, further comprising:
opposing jaws that form part of the end effector; and
a knife drive system arranged at the distal end of the shaft and including a knife,
wherein the at least one drive cable is operatively coupled to the knife drive system and operation of the accumulator system acts on the at least one drive cable to advance or retract the knife along the opposing jaws.

5. The robotic surgical tool of claim 1, wherein the at least one drive cable is routed from the shaft, through the one or more accumulator pulleys, and back to the shaft, and
wherein rotation of the bevel gear in a first angular direction pays in a portion of the at least one drive cable from the shaft, and rotation of the bevel gear in a second angular direction pays out a portion of the at least one drive cable to the shaft.

6. The robotic surgical tool of claim 5, wherein the bevel gear comprises a first bevel gear and the one or more accumulator pulleys comprise one or more first accumulator pulleys, the accumulator system further comprising:
a second bevel gear laterally offset from the first bevel gear and arranged to intermesh with the beveled pinion gear;
one or more second accumulator pulleys rotatably coupled to the second bevel gear,
wherein the at least one drive cable is routed from the shaft, through the one or more first and second accumulator pulleys, and back to the shaft, and
wherein rotation of the beveled pinion gear causes the first and second bevel gears to rotate in opposite angular directions.

7. The robotic surgical tool of claim 5, wherein the one or more accumulator pulleys comprise one or more first accumulator pulleys and one or more second accumulator pulleys, and the at least one drive cable comprises first and second drive cable portions extending distally along the shaft, and wherein rotation of the beveled pinion gear in a first direction pays in a length of the first drive cable portion to the one or more first accumulator pulleys from the shaft, and simultaneously pays out a length of the second drive cable portion from the one or more second accumulator pulleys to the shaft.

8. The robotic surgical tool of claim 1, wherein the beveled pinion gear comprises a first beveled pinion gear, the bevel gear comprises a first bevel gear, the at least one drive cable comprises first and second drive cables, the one or more accumulator pulleys comprise one or more first accumulator pulleys, and the drive input comprises a first drive input, the accumulator system further comprising:
the first beveled pinion gear coupled to the first drive input;
the first bevel gear arranged to intermesh with the first beveled pinion gear;
a second beveled pinion gear coupled to a second drive input rotatably mounted to the handle;
a second bevel gear arranged to intermesh with the second beveled pinion gear; and
the one or more first accumulator pulleys rotatably coupled to the first bevel gear, and one or more second accumulator pulleys rotatably coupled to the second bevel gear,
wherein the first drive cable is routed from the shaft, through the one or more first accumulator pulleys, and back to the shaft, and the second drive cable is routed from the shaft, through the one or more second accumulator pulleys, and back to the shaft, and
wherein rotation of the first bevel gear in a first angular direction pays in a portion of the first drive cable from the shaft, and rotation of the second bevel gear in a second angular direction pays out a portion of the second drive cable to the shaft.

9. A method of operating a robotic surgical tool, comprising:
actuating a drive input of a robotic surgical tool, the robotic surgical tool having an elongate shaft extending through a handle that provides the drive input, an accumulator system housed within the handle and operatively coupled to the drive input, and at least one drive cable threaded through the accumulator system and extending distally along the shaft, the accumulator system including:
a beveled pinion gear coupled to the drive input;
a bevel gear arranged to intermesh with the beveled pinion gear and rotatable about an axle;
a center accumulator pulley rotatably mounted to the bevel gear at the axle;
one or more outer accumulator pulleys rotatably mounted to the bevel gear near an outer periphery of the bevel gear;
operating the accumulator system by actuating the drive input and thereby moving the at least one drive cable along the shaft and altering at least one of a length or a force in the at least one drive cable; and
operating an end effector arranged at a distal end of the shaft with movement of the at least one drive cable.

10. The method of claim 9, wherein the handle is matable with an instrument driver arranged at an end of a robotic arm and the instrument driver provides a drive output, and wherein actuating the drive input comprises actuating the drive output mated with the drive input.

11. The method of claim 9, wherein the robotic surgical tool further includes an articulable wrist interposing the end effector and the distal end of the shaft and the at least one drive cable is operatively coupled to the wrist, and wherein operating the end effector further comprises:
placing tension on the at least one drive cable via operation of the accumulator system; and
articulating the end effector based on the tension assumed by the at least one drive cable.

12. The method of claim 9, wherein the robotic surgical tool further includes opposing jaws that form part of the end effector and a knife drive system arranged at the distal end of the shaft and including a knife, and wherein operating the end effector further comprises:
placing tension on the at least one drive cable via the accumulator system, the at least one drive cable being operatively coupled to the knife drive system; and
advancing or retracting the knife along the opposing jaws based on the tensile load assumed by the at least one drive cable.

13. The method of claim 9, wherein operating the accumulator system comprises:
rotating the beveled pinion gear as the drive input rotates;
rotating the bevel gear with rotation of the beveled pinion gear, wherein the at least one drive cable is routed from the shaft, through the one or more accumulator pulleys, and back to the shaft; and
drawing in a portion of the at least one drive cable from the shaft and simultaneously dispensing a portion of the at least one drive cable to the shaft as the bevel gear rotates.

14. The method of claim 9, further comprising moving the shaft relative to the handle while simultaneously operating the accumulator system.

* * * * *